(12) United States Patent
Van de Wardt et al.

(10) Patent No.: US 10,758,745 B2
(45) Date of Patent: Sep. 1, 2020

(54) METHODS AND SYSTEMS FOR BRACHYTHERAPY PLANNING BASED ON IMAGING DATA

(71) Applicant: NUCLETRON OPERATIONS B.V., Veenendaal (NL)

(72) Inventors: Cor Van de Wardt, Veenendaal (NL); Paulus Cornelis Hendrikus Maria Krechting, Veenendaal (NL); Jan Frans Lodewijk De Becker, Veenendaal (NL); Nicole Nesvacil, Wiener Neustadt (AT); Christian Kirisits, Vienna (AT); Richard Pötter, Vienna (AT); Maximilian Paul Schmid, Vienna (AT)

(73) Assignee: NUCLETRON OPERATIONS B.V., Veenendaal (NL)

( * ) Notice: Subject to any disclaimer, the term of this patent is extended or adjusted under 35 U.S.C. 154(b) by 871 days.

(21) Appl. No.: 15/312,978

(22) PCT Filed: May 28, 2015

(86) PCT No.: PCT/IB2015/001375
§ 371 (c)(1),
(2) Date: Nov. 21, 2016

(87) PCT Pub. No.: WO2015/181632
PCT Pub. Date: Dec. 3, 2015

(65) Prior Publication Data
US 2017/0120072 A1 May 4, 2017

Related U.S. Application Data

(60) Provisional application No. 62/003,776, filed on May 28, 2014.

(51) Int. Cl.
*A61N 5/10* (2006.01)
*A61B 6/00* (2006.01)
(Continued)

(52) U.S. Cl.
CPC ............ *A61N 5/103* (2013.01); *A61B 6/12* (2013.01); *A61B 6/4417* (2013.01); *A61B 8/085* (2013.01);
(Continued)

(58) Field of Classification Search
CPC ......... A61B 5/055; A61B 8/12; A61B 8/4461; A61B 8/483; A61B 8/4254; A61N 2/00; A61N 2/02; A61N 2/004
(Continued)

(56) References Cited

U.S. PATENT DOCUMENTS

2001/0041838 A1    11/2001  Holupka et al.
2003/0065260 A1*   4/2003   Cheng ................. A61B 8/0833
                                                           600/427
(Continued)

OTHER PUBLICATIONS

Chinese Official Action dated Nov. 19, 2018 issued in Chinese Application No. 201580016897.X.
(Continued)

*Primary Examiner* — Samuel G Gilbert
(74) *Attorney, Agent, or Firm* — Finnegan, Henderson, Farabow, Garrett & Dunner LLP

(57) ABSTRACT

Systems and methods for generating a radiation therapy treatment plan by using ultrasound images are disclosed. The method includes obtaining a first set of image data representing a first image of an anatomical region that includes a treatment applicator inserted into the anatomical region. The method further includes receiving tracking information indicating a position of the treatment applicator as represented in the first set of image data, obtaining a (Continued)

second set of image data representing a second image of the anatomical region, and combining at least a portion of the first set of image data with the second set of image data. One of the first set and the second set of image data is used to identify a target tissue portion in the anatomical region. The method further includes generating, based on the combined image data, treatment plan information for treating the target tissue portion in the anatomical region.

29 Claims, 16 Drawing Sheets

(51) Int. Cl.
    *A61B 8/12*     (2006.01)
    *A61B 8/00*     (2006.01)
    *A61B 6/12*     (2006.01)
    *A61B 8/08*     (2006.01)
    *A61B 34/20*     (2016.01)
    *A61B 90/00*     (2016.01)
    *A61B 18/00*     (2006.01)
    *A61B 17/00*     (2006.01)
(52) U.S. Cl.
    CPC .............. *A61B 8/0841* (2013.01); *A61B 8/12* (2013.01); *A61B 8/4218* (2013.01); *A61B 8/4245* (2013.01); *A61B 8/4416* (2013.01); *A61B 34/20* (2016.02); *A61B 90/37* (2016.02); *A61N 5/1016* (2013.01); *A61N 5/1027* (2013.01); *A61N 5/1049* (2013.01); *A61B 8/483* (2013.01); *A61B 2017/00274* (2013.01); *A61B 2018/00333* (2013.01); *A61B 2018/00547* (2013.01); *A61B 2018/00559* (2013.01); *A61B 2034/2055* (2016.02); *A61B 2034/2059* (2016.02); *A61B 2090/363* (2016.02); *A61B 2090/364* (2016.02); *A61B 2090/3784* (2016.02); *A61N 2005/1018* (2013.01); *A61N 2005/1051* (2013.01); *A61N 2005/1058* (2013.01); *A61N 2005/1059* (2013.01); *A61N 2005/1061* (2013.01)
(58) Field of Classification Search
    USPC .................. 600/1, 3, 424, 427, 439; 128/922
    See application file for complete search history.

(56) References Cited

U.S. PATENT DOCUMENTS

| | | |
|---|---|---|
| 2004/0225174 A1 | 11/2004 | Fuller et al. |
| 2009/0198094 A1 | 8/2009 | Fenster et al. |
| 2011/0178389 A1* | 7/2011 | Kumar .................. A61B 5/055 600/411 |
| 2013/0102891 A1 | 4/2013 | Binnekamp et al. |
| 2013/0204072 A1 | 8/2013 | Verard et al. |
| 2016/0310760 A1* | 10/2016 | Bharat ................ A61N 5/1038 |

OTHER PUBLICATIONS

International Search Report and Written Opinion in PCT/IB2015/001375, dated Nov. 9, 2015.

* cited by examiner

METHODS AND SYSTEMS FOR BRACHYTHERAPY PLANNING BASED ON IMAGING DATA

CROSS-REFERENCE TO RELATED APPLICATIONS

This application is a national phase of International Application No. PCT/IB2015/001375, filed on May 28, 2015, which claims the benefit of priority based on U.S. Provisional Patent Application No. 62/003,776, filed May 28, 2014. The entire contents of the above-referenced applications are expressly incorporated herein by reference.

TECHNICAL FIELD

The present disclosure relates generally to methods for radiation therapy treatment and, more particularly, to methods for brachytherapy planning using imaging data, such as ultrasound and CT images.

BACKGROUND

Brachytherapy treatment systems may treat a patient by inserting a hollow treatment device (aka "applicator") into or close to a patient's target tissue, such as a prostate gland, a breast, a cervix, or other accessible areas in which a tumor is located. The treatment applicators are connected outside the patient's body with an after-loading apparatus having a radiation delivery unit for advancing one or more energy emitting sources through the catheters, which deliver doses of radiation to the patient's target tissue.

A successful brachytherapy treatment may require careful planning to determine the location and boundary of the target tissue within the patient. In addition, the radiation dose applied to the patient via the applicator may need to be carefully controlled to effectively treat the cancerous cells, while limiting the exposure of adjacent tissues or organs to undesired levels of radiation.

Conventional brachytherapy planning systems may use computed tomography (CT) or magnetic resonant imaging (MRI) to visualize the target tissues and the surrounding organs of the patient for purpose of treatment planning. For example, CT images may be acquired from the patient after the applicator is placed in the patient. The CT images may be used to determine the location of the applicator's position relative to the patients' anatomy and to delineate organs at risk and target tissue (e.g., tumor delineation). However, tumor delineation may be difficult on CT images due to poor soft tissue contrast and thus introduce uncertainties in treatment planning. Although MRI images may provide high-contrast information and allow easy visualization of the target tissues, MRI equipment and procedures are expensive and may not be available to many patients.

Therefore, there exists a need for the development of tools to improve the quality, increase the accessibility, and reduce the costs of the brachytherapy procedure.

SUMMARY

The present disclosure provides improved systems and methods for providing brachytherapy planning using ultrasound images.

In an exemplary embodiment, a method for generating a radiation therapy treatment plan by using ultrasound images is disclosed. The method comprises obtaining, via an ultrasound device, a first set of image data representing a first image of an anatomical region. The anatomical region includes a treatment applicator inserted into the anatomical region. The method further comprises receiving tracking information indicating a position of the treatment applicator as represented in the first set of image data, obtaining a second set of image data representing a second image of the anatomical region, and combining at least a portion of the first set of image data with the second set of image data based on the position of the treatment applicator. One of the first set and the second set of image data is used to identify a target tissue portion in the anatomical region. The method further comprises generating, based on the combined image data, treatment plan information for treating the target tissue portion in the anatomical region.

In an exemplary embodiment, a system for generating a radiation therapy treatment plan by using ultrasound images is disclosed. The system comprises an ultrasound device, a tracking device, and a processor. The ultrasound device is configured to generate a first set of image data representing a first image of an anatomical region. The anatomical region includes a treatment applicator inserted into the anatomical region. The tracking device is configured to generate tracking information indicating a position of the treatment applicator as represented in the first set of image data. The processor is configured to obtain the first set of image data from the ultrasound device, receive the tracking information from the tracking device, obtain, from an imaging device, a second set of image data representing a second image of the anatomical region, and combine at least a portion of the first set of image data with the second set of image data based on the position of the treatment applicator. The combined image data is used to identify a target tissue portion in the anatomical region. The processor is further configured to generate, based on the combined image data, treatment plan information for treating the target tissue portion in the anatomical region.

In an exemplary embodiment, a non-transitory computer-readable medium is disclosed. The computer-readable medium stores instructions, which, when executed by a processor, cause the processor to perform a method for generating a radiation therapy treatment plan by using ultrasound images. The method comprises obtaining, via an ultrasound device, a first set of image data representing a first image of an anatomical region. The anatomical region includes a treatment applicator inserted into the anatomical region. The method further comprises receiving tracking information indicating a position of the treatment applicator as represented in the first set of image data, obtaining a second set of image data representing a second image of the anatomical region, and combining at least a portion of the first set of image data with the second set of image data based on the position of the treatment applicator. One of the first set and the second set of image data is used to identify a target tissue portion in the anatomical region. One of the first set and the second set of image data is used to identify organs at risk. The treatment applicator may be at least partially identified in each of the first set and the second set of image data to enable treatment applicator reconstruction in each of the first and second sets of image data. The method further comprises generating, based on the combined image data, treatment plan information for treating the target tissue portion in the anatomical region.

BRIEF DESCRIPTION OF THE DRAWINGS

The accompanying drawings, which are incorporated in and constitute a part of this specification, illustrate several embodiments of the present disclosure and together with the description, serve to explain the principles of the disclosed embodiments.

DETAILED DESCRIPTION OF THE EMBODIMENTS

Reference will now be made in detail to exemplary embodiments, examples of which are illustrated in the accompanying drawings. Wherever possible, the same reference numbers will be used throughout the drawings to refer to the same or like parts.

Systems consistent with the disclosed embodiments may use a first set of patient image data, such as ultrasound image data, to determine the location and boundary of target tissues (also called the target volume) within a patient. Embodiments consistent with the invention may also combine the first set of patient image data with a second set of patient image data, subsequently acquired from the patient, so as to provide treatment planning information for a radiation therapy, such as brachytherapy.

According to example embodiments of the disclosure, an imaging device acquires a first set of patient image data including an ultrasound image of an anatomical region of a patient showing a treatment applicator, such as a brachytherapy applicator, a needle, or other implant devices, inserted into or on the patient. The patient here may be a human or other animals. A three-dimensional position of the treatment applicator is tracked during the acquisition of the ultrasound image data, so that a location of the treatment applicator in the ultrasound image data may be determined. Thereafter, another imaging device may acquire a second set of patient image data, such as CT image data, of the region of the patient with the treatment applicator remaining therein. Systems consistent with the invention may therefore allow for determination of a location of the treatment applicator in the second set of patient image data based on an identification of the treatment applicator in the second set of patient image data, for example, based on operator input.

The first image data may then be combined with the second image data by aligning a graphical representation of the treatment applicator in the first image data and a graphical representation of the treatment applicator in the second image data. In this way, systems consistent with the invention enable generation of treatment planning information based on the combined image data. Compared with conventional treatment planning techniques, the systems disclosed herein may provide improved visualization of the target tissues. By using ultrasound images, the disclosed systems may provide a convenient, accessible, and low-cost method for examining the patient and planning the radiation therapy treatment, while also providing additional information for target contouring to physicians.

Figure 1:
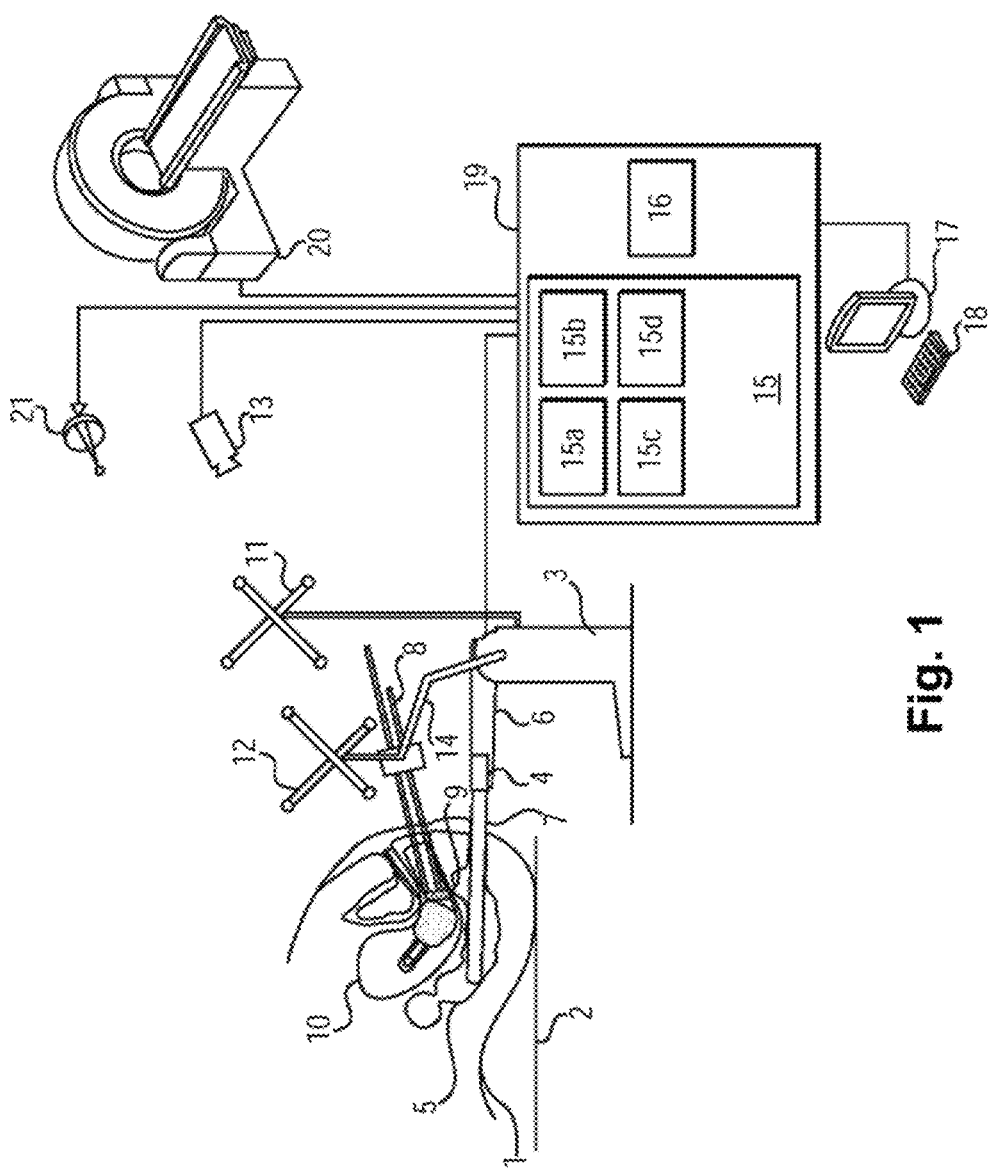
FIG. 1 depicts an exemplary radiation therapy system including a radiation therapy treatment planning system, according to an embodiment.

FIG. 1 shows an exemplary diagram of a radiation therapy treatment planning system, according to an embodiment. A patient 1 is shown placed on a table 2. Also shown is a base 3 for manipulating and immobilization of probes, treatment applicators, and/or trackers (e.g., markers), as described in further detail below. While in FIG. 1 base 3 is shown as mounted on a floor, base 3 may be mounted to other parts of the system, such as having base 3 mounted on top of table 2, a cart, a ceiling, or other points or structures in the three-dimensional space. In either event, table 2 and/or base 3 may be adjustable, so that the relative position between patient 1 and base 3 may be set by a user. Table 2 and base 3 may be adjusted manually or through drive means included therein.

An imaging device 7, such as an ultrasound device, may be mounted to base 3 through an extension arm 6. Extension arm 6 may be coupled to base 3 through a rotational joint that allows imaging device 7 to be adjusted with respect to base 3 in any direction as desired. Imaging device 7 may be a trans-rectal ultrasound device that may be inserted or placed in an internal cavity of a patient, such as a rectum 5, when acquiring image data from the patient. Imaging device 7 may also be a transabdominal ultrasound device that may be placed on a patient's abdomen when acquiring image data from the patient. Imaging device 7 may obtain a first set of patient image data including ultrasound images of the patient. The ultrasound images may be presented on a display device and provide sufficient soft-tissue contrasts, so that the target tissue may be visually or automatically distinguished from the surrounding tissues and organs.

The system may further include a treatment applicator 9, such as a brachytherapy applicator, needle, or other implant devices, for delivering a radiation source to the patient. Applicator 9 may include one or more needles or catheters 8, which may receive the radiation source from an afterloading system (not shown), as known in the art. The radiation source may include, for example, radioactive source that may be delivered and placed in the patient through applicator 9. The specific type of applicator 9 used for the treatment may depend on the type of cancer being treated and the characteristics of the target tumor. For example, for cervical cancer, the system may use a tandem-and-ovoid applicator, which includes round hollow holders that are placed inside the patient's uterus to provide treatment. Alternatively, the system may use a tandem-and-ring applicator for the cervical cancer. The system may, however, use other types of applicators known in the art for treating other types of cancers.

During treatment planning, applicator 9 may be inserted in patient 1 through, for example, a vagina and placed in a uterus 10 of the patient. Applicator 9 may then be affixed to the patient by, for example, gauze packing, stitching, or clamping. Applicator 9 may be further affixed to base 3 or table 2 through a supporting structure 14, which may be an arm or strut. Supporting structure 14 provides structural support for applicator 9 and maintains a fixed spatial relationship between device 7 and applicator 9 during the acquisition of the ultrasound image data.

The system may further include a tracking device or subsystem for tracking the positions of ultrasound device 7 and treatment applicator 9 during the acquisition of the first set of patient image data, such as the ultrasound image data. For example, the tracking device may track the positions of device 7 and device 9 with respect to each other. Alternatively, the tracking device may track the positions of device 7 and device 9 with respect to a reference, which may be an absolute reference, such as the operation room, or a relative reference, such as the table or the base. The positions of device 7 and device 9 may allow subsystem 19 to further determine the relative positions of device 7 and device 9. The tracking device may include a marker 11 attached to ultrasound device 7, extension arm 6, or base 3. The tracking device may further include a marker 12 attached to applicator 9 or catheter 8.

Markers 11 and 12 may include physical features that may be used to indicate three-dimensional positions of device 7 and applicator 9. In one embodiment, camera 13 may generate image or video data of markers 11 and 12. Alternatively, markers 11 and 12 may emit optical, electrical, or magnetic signals, or the like, which may be received by a signal receiver 21, which generate positional data based on the signals. Subsystem 19 may receive tracking information from camera 13 or receiver 21, including the image, video, or positional data and track the three-dimensional positions of device 7 and applicator 9.

Additionally, the ultrasound device may be connected to a motor 4 having an encoder configured to drive device 7 to rotate during the acquisition of the ultrasound image data. Motor 4 and the encoder may be disposed within extension arm 6 and provide tracking information of the position or rotational angle of device 7. The encoder position may also be used in combination with the two dimensional acquired ultrasound data to guide the reconstruction of the three-dimensional ultrasound data from the two dimensional ultrasound data.

Alternatively, imaging device 7 may include a marker or signal emitter disposed thereon. The marker or signal emitter may be tracked by camera or signal receiver 21, which provides the tracking information to subsystem 19 to determine the position or rotational angle of imaging device 7. Other known techniques may also be used to provide the tracking information to track the three-dimensional positions of device 7 and applicator 9 and the rotational angle of device 7.

Still alternatively, imaging device 7 may be a three-dimensional (3D) ultrasound device or a matrix device that may be configured to generate three-dimensional ultrasound image data without the motor. In this embodiment, image device 7 may include internal tracking system configured to provide the tracking information to subsystem 19 to determine the position of a particular imaging plane in the three-dimensional ultrasound image data.

The system may further include treatment processing subsystem 19, which communicates with device 7 and the tracking device. Subsystem 19 may receive, from imaging device 7, the first set of patient image data representing ultrasound images of the patient. Subsystem 19 may then store the first image data in a memory 15, analyze the first image data using processor 16, and present the ultrasound images to a user through a display device 17.

Subsystem 19 may receive from the tracking device the tracking information representing the corresponding positions of device 7 and applicator 9. Subsystem 19 may analyze the tracking information and automatically determine the three-dimensional positions of device 7 and applicator 9 and the rotational angle of device 7. Based on the positions of device 7 and applicator 9, along with the rotational angle of device 7, subsystem 19 may further define a three-dimensional coordinate system associated with applicator 9 and calculate the three-dimensional coordinates (e.g., x, y, and z) of each image data point with respect to applicator 9 based on the coordinate system.

Subsystem 19 may also receive, from an input device 18, user inputs that represent selections or indications of image features in the ultrasound image data. For example, input device 18 may allow a user to identify the target tissue in the ultrasound image data by outlining a boundary of the target tissue in the ultrasound image presented on display device 17. Input device 18 may also allow a user modify after the automatic identification of the location of applicator 9 in the ultrasound image data by selecting one or more data points on display device 17.

Subsystem 19 may further receive a second set of patient image data from an imaging device 20, such as a CT device, an MRI device, an X-ray device, and the like. As further described below, subsystem 19 may combine the first set of patient image data acquired through device 7 and the second set of patient image data acquired through imaging device 20, and then generate treatment planning information based on the combined patient image data.

In some embodiments, subsystem 19 may include one or more devices or systems that may or may not be co-located in a single treatment area or room. For example, in one embodiment, ultrasound image acquisition may occur in the operating room where the treatment applicator is inserted, but image processing or contouring (e.g., target delineation, applicator reconstruction, etc.) may be performed in a separate room, such as a treatment planning room. Indeed, presently contemplated embodiments include a variety of configurations, not limited to all the components of subsystem 19 being located in a single area or room.

Imaging device 20 and imaging device 7 may be located in different facilities, so that the patient is transported between imaging device 7 (e.g., the ultrasound system) and device 20 (e.g., the CT system) in order to acquire the first set of patient image data and the second set of patient image data. Alternatively, imaging device 20 and imaging device 7 may be co-located, so that the first set of patient image data and the second set of patient image data may be acquired at a single location without transporting the patient. For example, imaging device 7 may be attached to the table of a CT device or the X-ray machine, such that the patient may be placed on the table to acquire both sets of patient image data. As such, transportation of the patient between facilities may be omitted.

According to an embodiment, memory 15 of subsystem 19 may be a storage medium known in the art, including a volatile or non-volatile memory, such as a ROM, a RAM, a flash drive, a hard drive, a CD-ROM, a DVD-ROM, a register, and the like. Memory 15 may store computer codes including computer-executable instructions relevant to the radiation therapy planning. Processor 16 may be a central processing unit (CPU) that is known in the art, such as an INTEL processor or an AMD processor. In an embodiment, the CPU may be a general purpose processor. Processor 16 may retrieve and execute the computer-executable instructions from storage medium 15, which may cause the processor 16 to perform the processes and operations disclosed herein.

The computer codes stored in memory 15 may include a plurality of program modules, such as an image acquisition and processing module 15a, a tracking module 15b, an image registration module 15c, and a treatment planning module 15d. The program modules may be designed in or by means of known techniques and programming languages, such as C #, Java, C++, HTML, XML, or HTML.

Image acquisition and processing module 15a may be configured to acquire and process the image data from imaging device 7 and imaging device 20. Module 15a may process the image data to identify the target tissue, the surrounding organs, and the treatment applicator in the patient image data and determine the locations and boundaries thereof. Alternatively, module 15a may also interact with a user through user input device 18 and receive user inputs that identify various image features, such as the boundaries of the target tissue, the surrounding organs, and the treatment applicator. Module 15a may apply known techniques, such as image filtering, edge detection, feature recognition, and the like to process the image data.

Tracking module 15b may be configured to receive tracking information from the tracking device and determine the positions of imaging device 7 and treatment applicator 9. For example, the tracking information may include video data received from camera 13 indicating positions of markers 11 and 12 associated with device 7 and treatment applicator 9, respectively. By analyzing the video data of markers 11 and 12, module 15b may determine the three-dimensional positions of device 7 and treatment applicator 9. As another example, the tracking information may be provided based on optical signals, magnetic signals, acoustic signals, electrical signals, and the like received from signal receiver 21. By analyzing these signals, module 15b may determine the positions of device 7 and treatment applicator 9. Based on the tracking information, module 15b may further determine the relative position between device 7 and treatment applicator 9.

Additionally, the tracking information may represent rotational signals received from the encoder of motor 14. Based on the tracking information from the encoder, module 15b may determine the rotational angle of imaging device 7. Alternatively, the rotational angle of imaging device 7 may be determined based on the tracking information received from camera 13 or signal receiver 21. For example, video data may be received from camera 13 representing images of the marker associated with the outer surface of imaging device 7. By analyzing the video data from camera 13, module 15b may determine the rotational angle of imaging device 7. As another example, signals may be received from signal receiver 21 including optical signals, electrical signals, acoustic signals, magnetic signals, and the like. Module 15b may analyze these signals to determine the rotational angle of imaging device 7.

Image registration module 15c may be configured to determine the locations of treatment applicator 9 in the first set of patient image data received from device 7 and in the second set of patient image data received from device 20. More specifically, module 15c may define a coordinate system associated with treatment applicator 9. Based on the positions of device 7 and treatment applicator 9 and the rotational angle of device 7 provided by tracking module 15b, module 15c may calculate the coordinates of each image element (e.g., each pixel, voxel, or the like) in the coordinate system associated with treatment applicator 9.

Similarly, module 15c may determine the coordinates of each image element in the second set of patient image data acquired from device 20 based on an identification of treatment applicator 9. Alternatively, device 20 may provide information on the coordinates of individual image elements through its own tracking system or inherent configurations.

Based on the locations of treatment applicator 9, module 15c may be configured to combine the first set of patient image data with the second set of patient image data. For example, module 15c may first align a graphical representation of treatment applicator 9 in the first set of patient image data and a graphical representation of treatment applicator 9 in the second set of patient image data. This may be accomplished by image processing techniques known in the art. For example, module 15c may select, in the respective images, a plurality of feature points corresponding to the treatment applicator 9. Module 15c may then register the graphical representations of treatment applicator 9 by aligning the feature points.

Once the graphical representations of treatment applicator 9 in the first set of patient image data and the second set of patient image data are registered with each other, module 15c may then convert the coordinates of the image elements from the first set of patient image data to the second set of patient image data, or vice versa Module 15c may then combine the first set of patient image data, or a portion thereof, with the second set of patient image data in the same coordinate system based on the registration of treatment applicator 9.

Treatment planning module 15d may be configured to generate treatment planning information based on the combined image data. For example, module 15d may cause display device 17 to display the combined image data with the treatment planning information to a user, such as a physician. The treatment planning information may indicate locations of the target tissue and the surrounding organs and their spatial relationship with treatment applicator 9. The treatment planning information may also include a graphical representation of a spatial distribution of the radiation to be delivered by treatment applicator 9. The graphical representations may provide visual information to aid a physician to estimate effects of the radiation treatment and plan the treatment accordingly. The treatment planning information generated by module 15d will be further discussed below.

Figure 2:
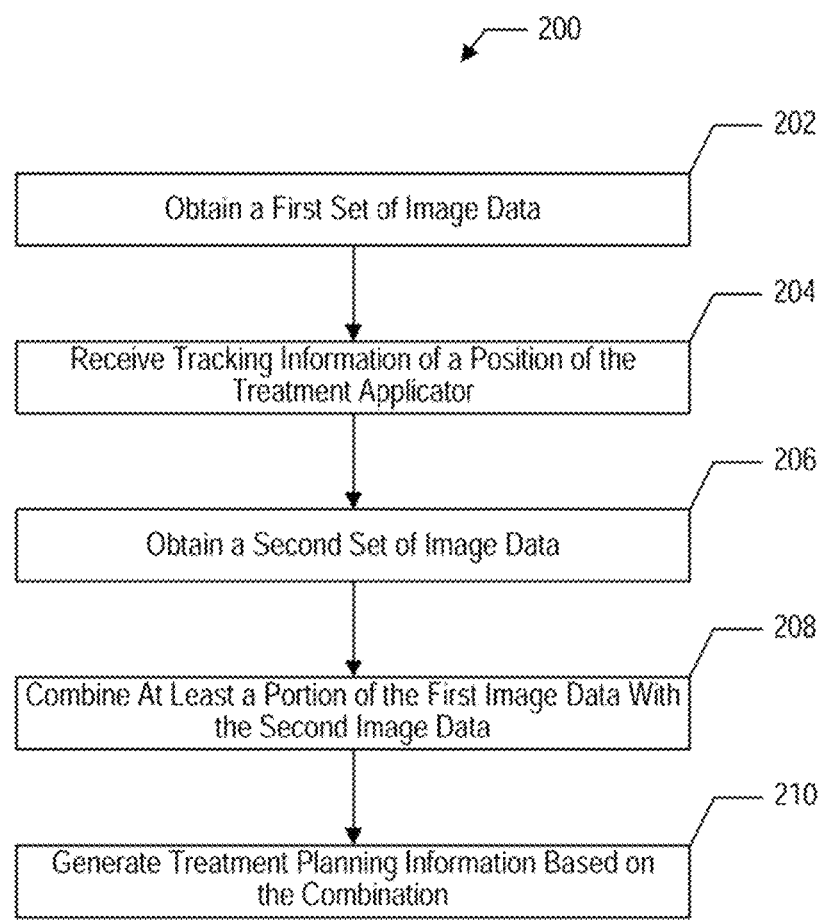
FIG. 2 depicts a flow chart of an exemplary process for radiation therapy treatment planning that may be applied to the system of FIG. 1, according to an embodiment.

FIG. 2 illustrates a flowchart of an exemplary process 200 for radiation therapy planning, according to an embodiment. Process 200 may be applied to or implemented in the radiation therapy treatment planning system of FIG. 1 and specifically by executing the program modules stored in subsystem system 19.

According to process 200, a first set of image data is obtained at step 202 by subsystem 19 through ultrasound device 7. In general, the first set of patient image data may provide improved soft tissue visualization and reflect high-contrast images of the target tissue. For example, the first set of image data may represent ultrasound images of a targeted region of the patient, such as a cervical region, a prostate region, or a breast region. The targeted region of the patient may include, for example, a target tissue, such as a cervical cancer, prostate cancer, a breast cancer, or the like, to which a radiation therapy, such as a brachytherapy, is to be applied. The targeted region of the patient may include a treatment applicator, such as a brachytherapy applicator or a catheter, located in an anatomical cavity of the patient in preparation for the radiation therapy.

Figure 6:
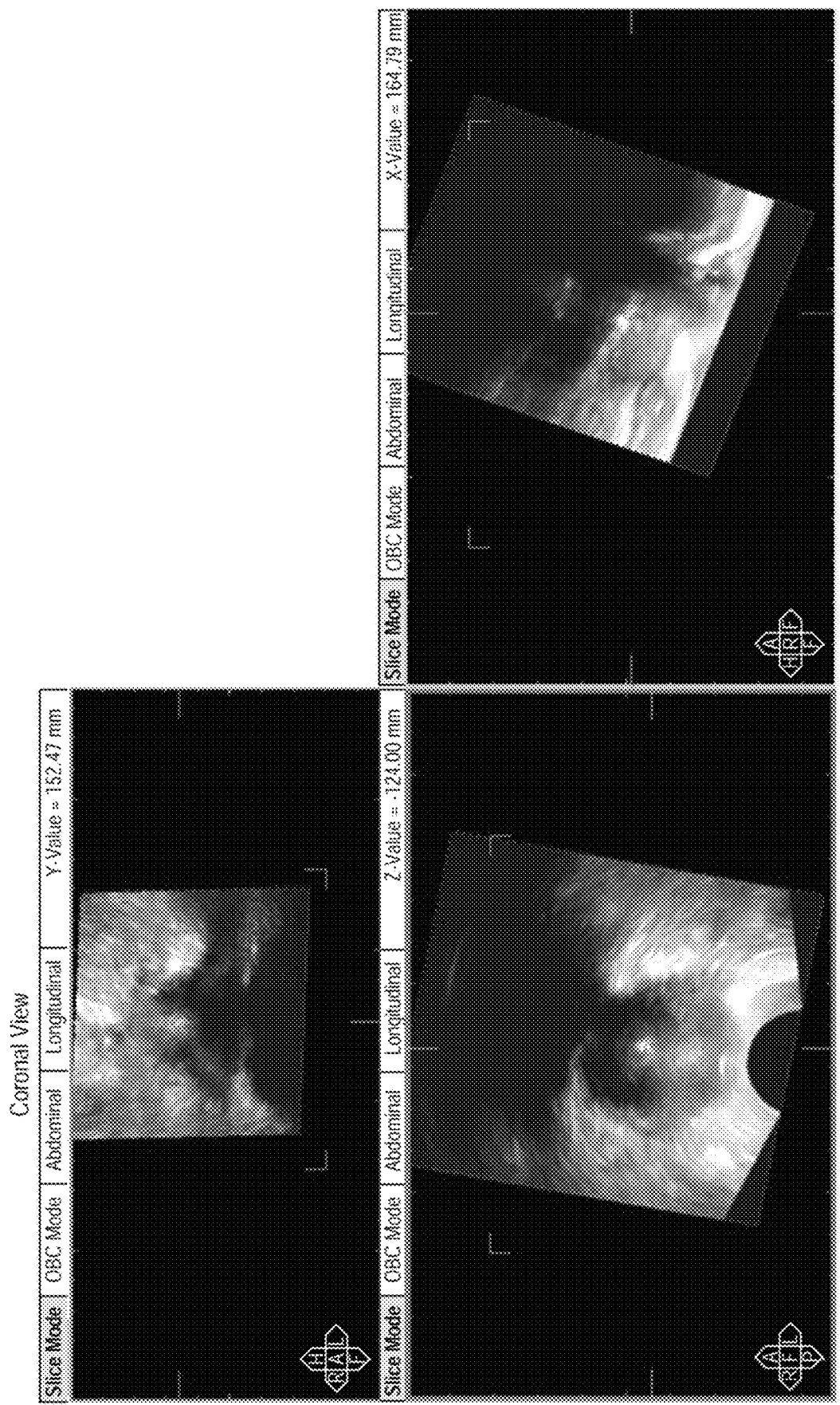
FIG. 6 depicts exemplary ultrasound image data acquired by the system of FIG. 1, according to an embodiment.

The first set of image data may include two-dimensional image data or three-dimensional image data. The first image data set may include a plurality of image elements, such as pixels or voxels, each of which includes a value that represents a physical property of the patient within the image element. In one embodiment, the first image data set may be acquired by the ultrasound device (e.g., device 7) at a trans-rectal position (e.g., inside the rectum). Alternatively, the ultrasound device may be placed at other locations inside or outside the patient. FIG. 6 illustrates an exemplary three-dimensional ultrasound image data acquired by the trans-rectal ultrasound device showing three views (coronal view, axial view, and sagittal view) of the cervical region of a patient. The ultrasound image data of FIG. 6 includes high-contrast images of the target tissue that allows an improved visualization of the target tissue within the cervical area of the patient.

The ultrasound device may be rotated during the acquisition to cover substantially the entire targeted region of the patient. For example, the ultrasound device may be driven by motor 4, which rotates the ultrasound device incrementally in a step-wise fashion.

During the acquisition of the first image data, the treatment applicator and the ultrasound device 7 may be affixed or immobilized to base 3, so that their three-dimensional positions remain unchanged. The ultrasound device 7 may be attached and affixed to base 3 through extension arm 6, while being rotated by motor 4. The treatment applicator may be affixed to base 3 through a supporting means, such as an arm, a strut, or a bar.

At step 204, the three-dimensional position of the treatment applicator is tracked during the acquisition of the first set of image data. As discussed above in connection with FIG. 1, the position of the treatment applicator may be tracked by the tracking device using marker 12 associated with the treatment applicator. The tracking device may include a camera that takes pictures or videos of marker 12 and transmits tracking information including the pictures or videos to subsystem 19 for analysis. Alternatively, the tracking device may include a signal receiver 21 that receives signals from marker 12 and transmits tracking information generated based on the signals to subsystem 19 for analysis. Subsystem 19 may then analyze the tracking information and determine the three-dimensional position of the treatment applicator.

Additionally, in the illustrated embodiment, at step 204, the three-dimensional position of the ultrasound device may also be tracked during the acquisition of the first image data. However, it should be noted that in other embodiments, the tracking information regarding a position of the treatment applicator may be received before or after obtaining the first set of image data at step 202. Similarly, ultrasound device 7 may be tracked by the tracking device using marker 11. Subsystem 19 may analyze the tracking information from the tracking device and determine the three-dimensional position of the ultrasound device.

Still additionally, at step 204, the rotational angle of the ultrasound device may be tracked during the acquisition of the first image data. The motor 4 used to rotate ultrasound device 12 may include an encoder that generates signals indicating the rotational angle of the ultrasound device. Subsystem 19 may receive tracking information from motor 4 including the signals and analyze the signals to determine the rotational angle of the ultrasound device.

Figure 7:
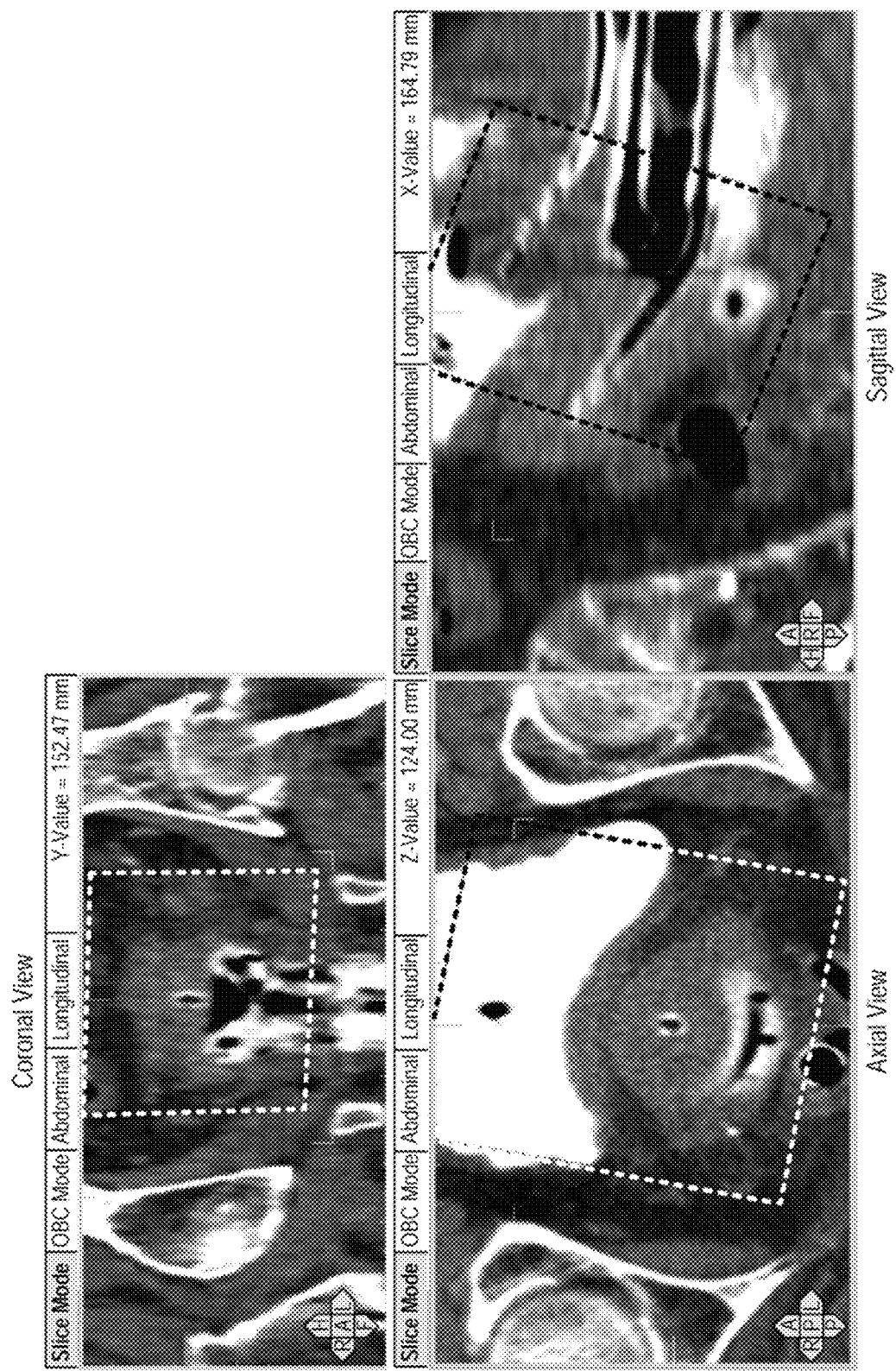
FIG. 7 depicts exemplary CT image data acquired after the ultrasound device is removed from the patient, according to an embodiment.

At step 206, a second set of image data is obtained by subsystem 19 from a second imaging device, such as a CT, an MRI, an X-ray, an ultrasound device, or the like. In general, the second image data may provide high-contrast images of tissues or organs surrounding the target tissue, but relatively poor contrast images of the target tissue itself. For example, the second set of image data may include CT image data that allows better visualization of rectum, bone, bladder, and the like. Additionally, the second set of image data may also include a high-contrast image of the treatment applicator, so that subsystem 19 may determine the location of the treatment applicator by analyzing the second image data. FIG. 7 illustrates exemplary CT images of the patient's cervical region generated based on the second set of image data. The CT images of FIG. 7 shows three views of the cervical region including high-contrast image features that correspond to the bone, rectum, and bladder of the patient. In addition, the CT images also show a high-contrast image of the brachytherapy applicator placed in the cervical area. The target tissue in the cervical area, however, is not clearly reflected in these CT images due to the poor soft tissue visualization.

At step 208, the first image data and the second image data may be combined based on registration of the treatment applicator. Step 208 may be carried out in multiple sub-steps, according to an embodiment. First, the location of the treatment applicator with respect to the first set of image data may be calculated by subsystem 19 based on the three-dimensional position of the treatment applicator, the three-dimensional position of the ultrasound device, and the rotational angle of the ultrasound device determined in step 204.

Figure 8:
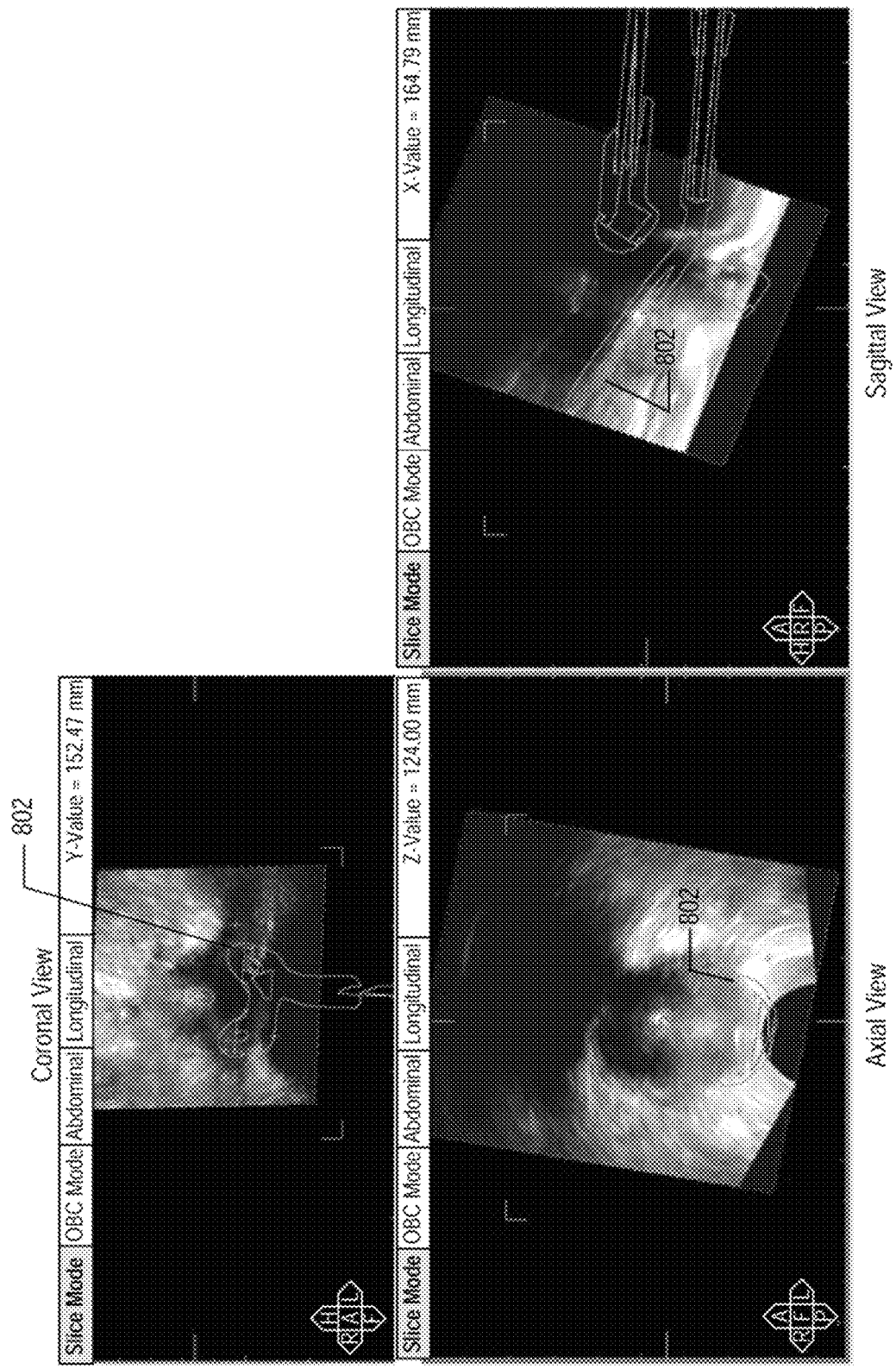
FIG. 8 depicts an identification of a treatment applicator in the ultrasound image data, according to an embodiment.

Based on the location of the treatment applicator with respect to the first set of image data, a graphical representation of the treatment applicator may be projected to the first set of image data. FIG. 8 illustrates an exemplary embodiment of the first image data with a graphical representation 802 of the treatment applicator projected thereto. The graphical representation of the treatment applicator may be a standard graphical template previously generated for treatment applicator 9 and stored in subsystem 19. FIG. 8 shows three views of the graphical representation of the treatment applicator and its spatial relationship with respect to the cervical region of the patient. According to another embodiment, subsystem 19 may allow a user to select a graphical representation of treatment applicator 9 from a plurality of graphical representations stored therein. Subsystem 19 may generate a list of graphical representations and prompt the user to select one from the list according to the treatment applicator to be used in the radiation therapy treatment.

Second, the first set of image data may be analyzed manually or automatically to determine the location and boundary of the target tissue and/or organs at risk, such as the rectum, bladder, bones, etc. In one embodiment, the location and boundary of the target tissue may be determined automatically by subsystem 19, which applies standard image analysis and recognition techniques to the first set of image data. Alternatively, subsystem 19 may display the first set of image data to a user through display device 17 and prompt the user to provide inputs that identify the location and boundary of the target tissue. For example, subsystem 19 may receive user inputs through a mouse that outline or delineate the boundary of the target tissue on display device 17. Display device 17 may also include a touch screen and allow the user to directly draw the boundary of the target tissue thereon. If the first set of image data is a three-dimensional data set of the patient, subsystem 19 may present the three-dimensional data set slide-by-slide and allow the user to identify the target tissue in all or a portion of the slides.

Figure 9:
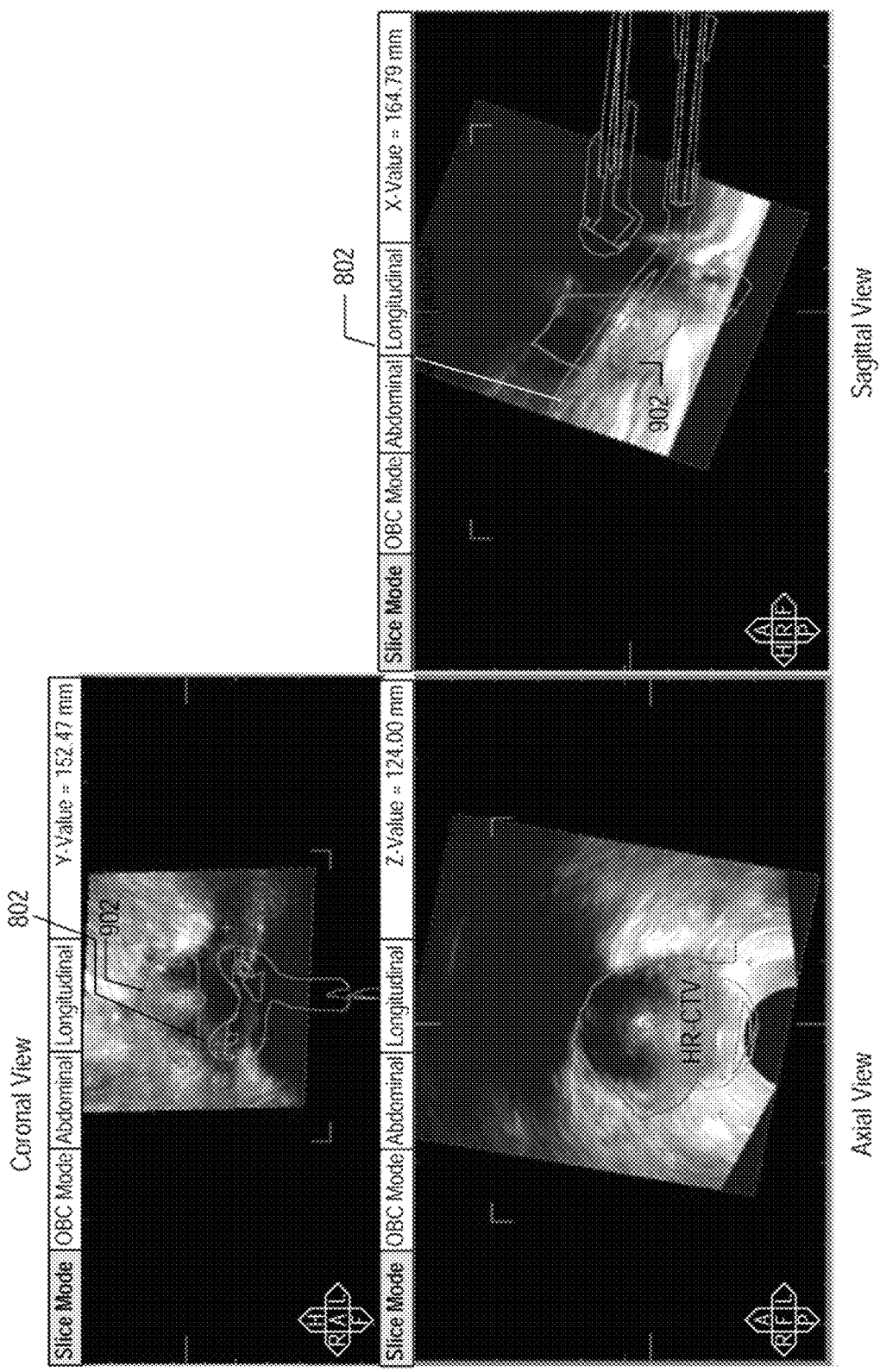
FIG. 9 depicts an identification of a target tissue and treatment applicator in the ultrasound image data, according to an embodiment.

FIG. 9 illustrates an exemplary embodiment of showing a graphical boundary 902 of the target tissue that module 15*a* identified based on the first image data. FIG. 9 also illustrates the spatial relationship between boundary 902 of the target tissue and graphical representation 802 of the treatment applicator. For example, the three views of the ultrasound image data show both graphical representation 802 of the treatment applicator and graphical boundary 902 of the target tissue identified by module 15*a*.

Third, the location of the treatment applicator with respect to the second set of image data may be determined. Subsystem 19 may automatically determine the location of the treatment applicator in the second set of image data by applying the standard image analysis and processing techniques.

Figure 10:
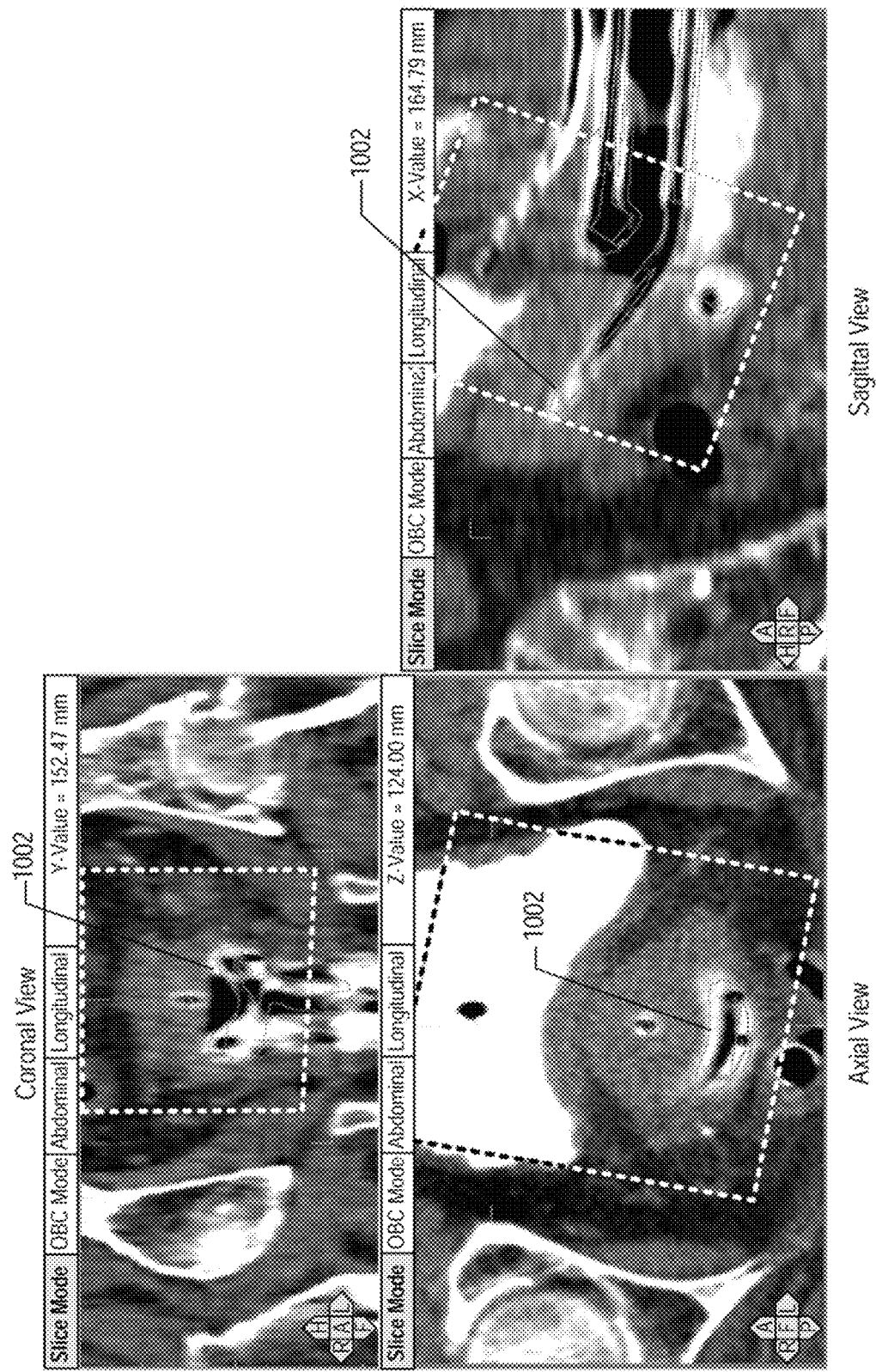
FIG. 10 depicts an identification of the treatment applicator in the CT image data, according to an embodiment.

Alternatively, subsystem 19 may present the second set of image data to the user through display device 17 and prompt the user to identify or outline the treatment applicator in the second set of image data. The user may provide the inputs that specify the location and boundary of the treatment applicator through a mouse, touch screen, and the like. For example, subsystem 19 may display the second image data on display device 17 to a user and allow the user to outline the treatment applicator thereon by using a mouse. Subsystem 19 may then determine the location of the treatment applicator based on the user input and project a graphical representation of the treatment applicator to the second image data. FIG. 10 illustrates an exemplary embodiment that shows three views of the second set of image data with a graphical representation of the treatment applicator projected thereto. Alternatively, subsystem 19 may allow a user to select a graphical representation from a list stored thereon for the treatment applicator and project the selected graphical representation to the displayed second image data.

Next, at step 208, the graphical representations of the treatment applicator in the first set of image data and the second set of image data are aligned or registered with each other. Subsystem 19 may do this automatically through use of standard image registration techniques that may align the graphical representations of the treatment applicator. Subsystem 19 may automatically align the graphical representations of the treatment applicator based on individual features points on the treatment applicator. For example, subsystem 19 may identify a feature point of the treatment applicator on each view of the first and second image data and then automatically align these respective images to create the combined image data by aligning or matching the corresponding features points of the treatment applicator. According to one embodiment, subsystem 19 may use three features to align the graphical representations of the treatment applicator.

Figure 11:
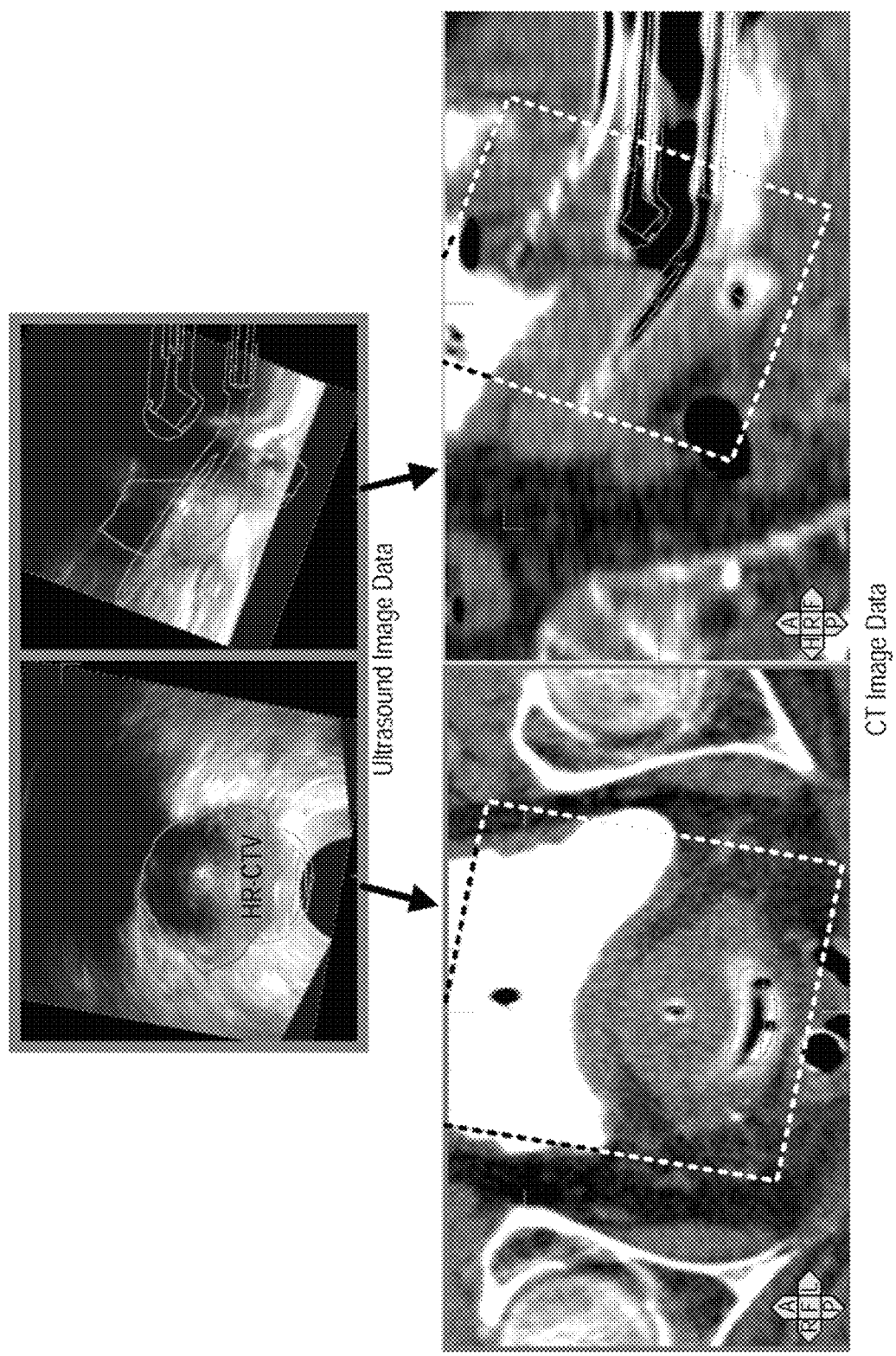
FIG. 11 depicts an exemplary process of combining the ultrasound image data with the CT image data based on the registration of the treatment applicator, according to an embodiment.

Alternatively, subsystem 19 may present the first set of image data and the second set of image data to the user through display device 17 and prompt the user to provide user inputs to align the graphical representations of the treatment applicator. FIG. 11 illustrates an exemplary embodiment presenting two views of the first set of image data (e.g., an ultrasound data set) and two views of the second set of image data (e.g., a CT data set) to the user. The user may then use the mouse or the touch screen to adjust one or both of the data sets so that the graphical presentations of the treatment applicator are aligned. Subsystem 19 may also present the feature points of the treatment applicator and prompt the user to align the feature points of the treatment applicator in the first and second sets of image data.

Finally, at step 208, the first set of image data and the second set of image data are combined based on the registration of the treatment applicator discussed above. Subsystem 19 may combine the image data sets by projecting the first set of image data to the second set of image data, or vice versa. Alternatively, subsystem 19 may combine the image data sets by projecting only a portion of the first set of image data, such as the boundary of the target tissue identified above based on the first set of image data, to the second set of image data.

Still alternatively, subsystem 19 may define a coordinate system including x, y, and z axes associated with the treatment applicator. Subsystem 19 may then calculate the coordinates of each image element (e.g., each pixel or voxel) in the first set of image data with respect to the treatment applicator. After the images of the treatment applicator are aligned, subsystem 19 may then recalculate the coordinates of the image elements in the first set of image data based on the rotations and translations of the graphical representations of the treatment applicator caused by the registration.

Figure 12:
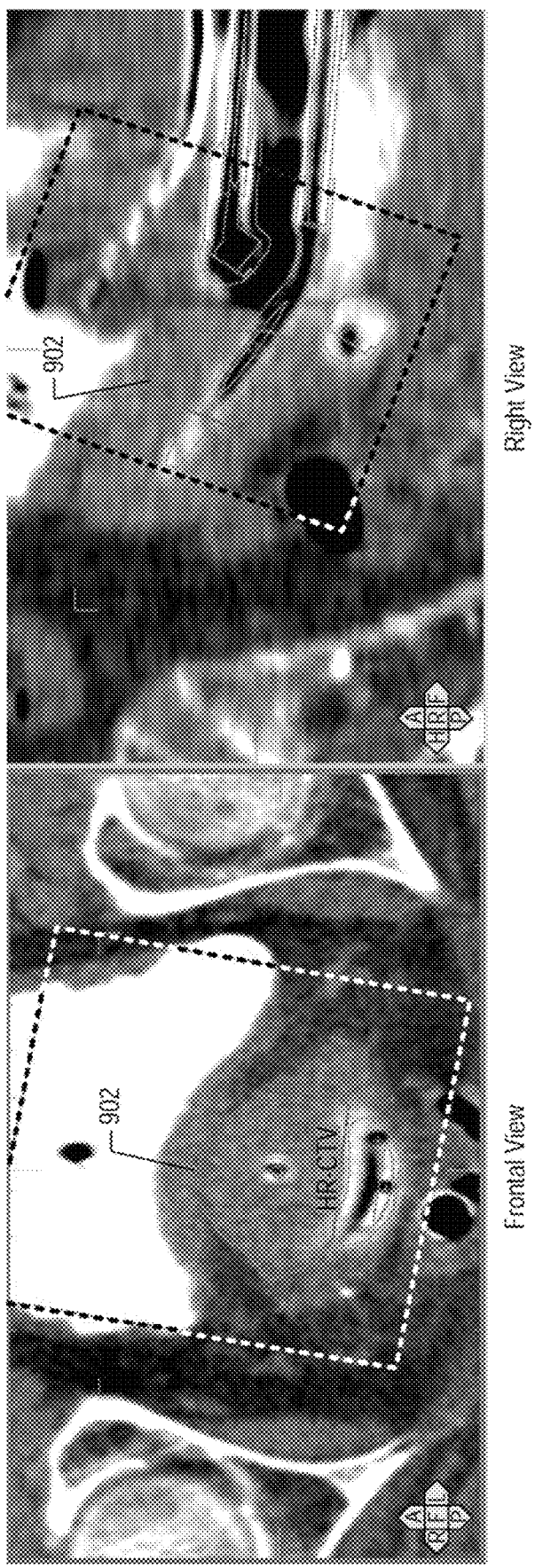
FIG. 12 depicts an exemplary combination of the ultrasound image data and the CT image data including a projection of a graphical boundary of the target tissue to the CT image data, according to an embodiment.

FIG. 12 illustrates an exemplary embodiment of the combination of the image data sets. FIG. 12 shows two views of the combination, in which the boundaries of the target tissue determined based on the first set of image data are projected onto the second set of image data. As shown in FIG. 12, the boundaries of the target tissue, which is difficult to visualize in the second set of image data due to poor soft tissue contrast, are delineated in the second set of image data. As a result, the combined image data provides an improved visualization of the spatial relationship between the target tissue and the surrounding tissues and organs.

At step 210, treatment planning information may be generated based on the combination of the first set of image data and the second set of image data discussed above. Subsystem 19 may first identify a group of organs surrounding the target tissue that are potentially at risk during the subsequent radiation therapy due to their proximity to the radioactive source placed in the target tissue. These organs are called organs at risk. Subsystem 19 may identify the boundaries of the organs at risk by analyzing the first set of image data and/or the second set of image data depending on which organ is relatively easier to be identified. Subsystem 19 may also present the first set of image data and the second set of image data to the user through display device 17 and prompt the user to provide user inputs to identify the boundaries of the organs at risk.

Figure 13:
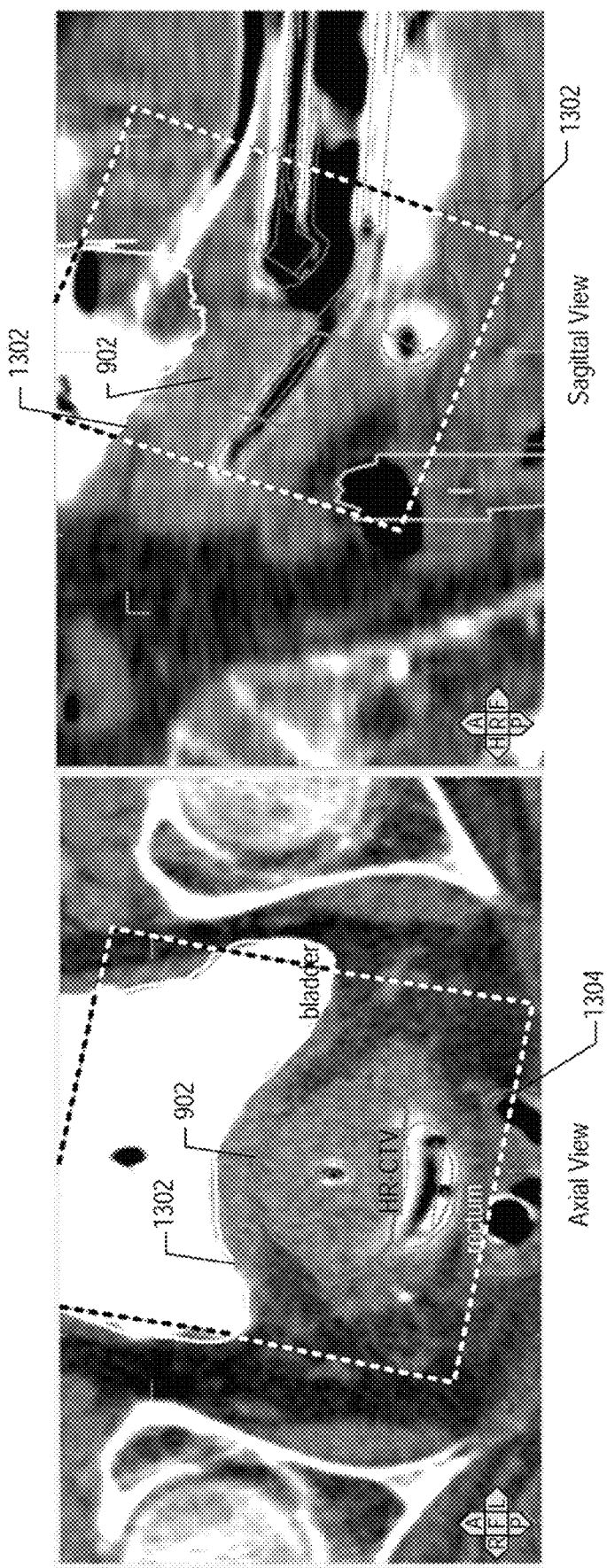
FIG. 13 depicts exemplary therapy planning information generated based on the combination of the ultrasound image data and the CT image data, including contours of organs at risk, according to an embodiment.

Additionally, subsystem 19 may project the boundaries of the organs at risk onto the combination of the image data sets. FIG. 13 illustrates an exemplary embodiment of the combined image data with the boundaries of various organs at risk projected thereto. FIG. 13 also shows the boundary of the target tissue and the graphical representation of the treatment applicator to provide visual information on the spatial relationship between the target tissue and the organs at risk.

Figure 14:
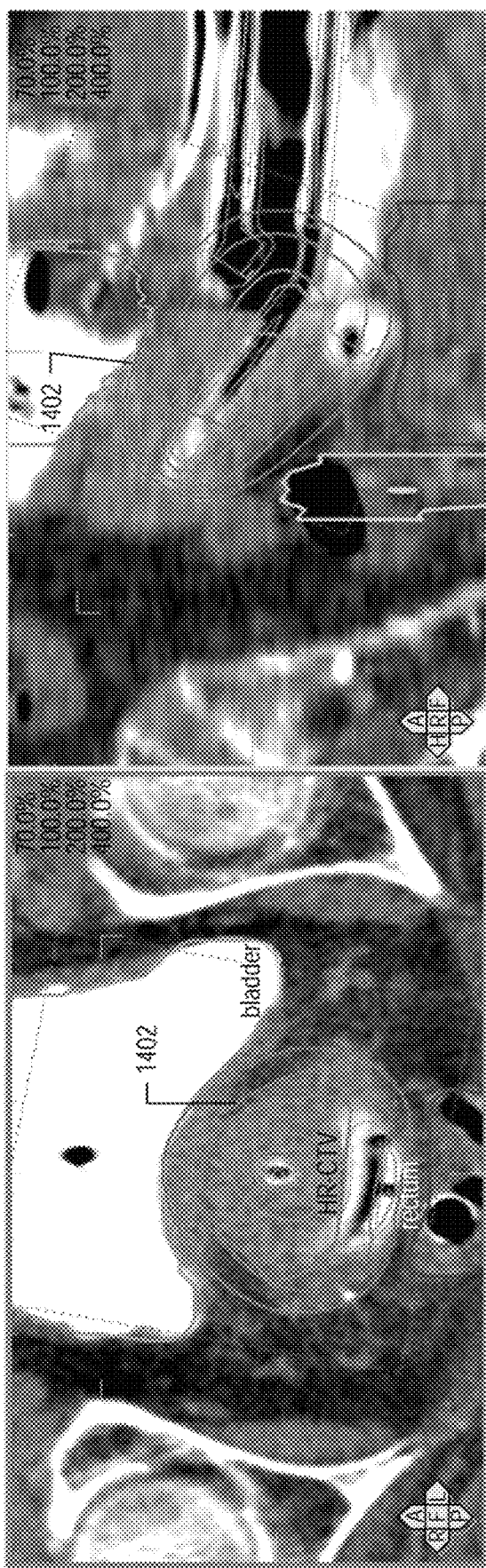
FIG. 14 depicts exemplary therapy planning information generated based on the combination of the ultrasound image data and the CT image data, according to an embodiment.

Still additionally, subsystem 19 may determine a spatial distribution of the radiation surrounding the target tissue during the planned radiation treatment. Subsystem 19 may then project a graphical model to the combined image data indicating the spatial. FIG. 14 illustrates an exemplary embodiment showing two views of the combined image data with the graphical model projected thereto. The graphical model may include concentric curves, each of which indicates a spatial distribution of the radiation that represent isodose lines of the radiation around the radiation source.

According to an alternative embodiment, subsystem 19 may use color codes in the graphical model, such as the curves shown in FIG. 14, to illustrate different radiation exposures corresponding to the isodose lines. For example, the isodose lines relatively further away from the radioactive center may be assigned a blue color indicating relatively low radiation exposures, while the isodose lines relatively close to the radioactive center may be assigned a red color indicating relatively high radiation exposures.

Accordingly, based on the combined image data and the treatment planning information generated by subsystem 19, the treatment planning system allows the user to visually determine the effectiveness of the planned radiation treatment. The treatment planning system may also allow the user to assess potential adverse effects on the surrounding organs after the radioactive source is placed in the target tissue. The treatment planning system may provide information to allow the user to adjust the parameters of the radiation treatment, such as the location, the orientation, or the dose of the radioactive source to be placed in the target tissue.

Figure 3:
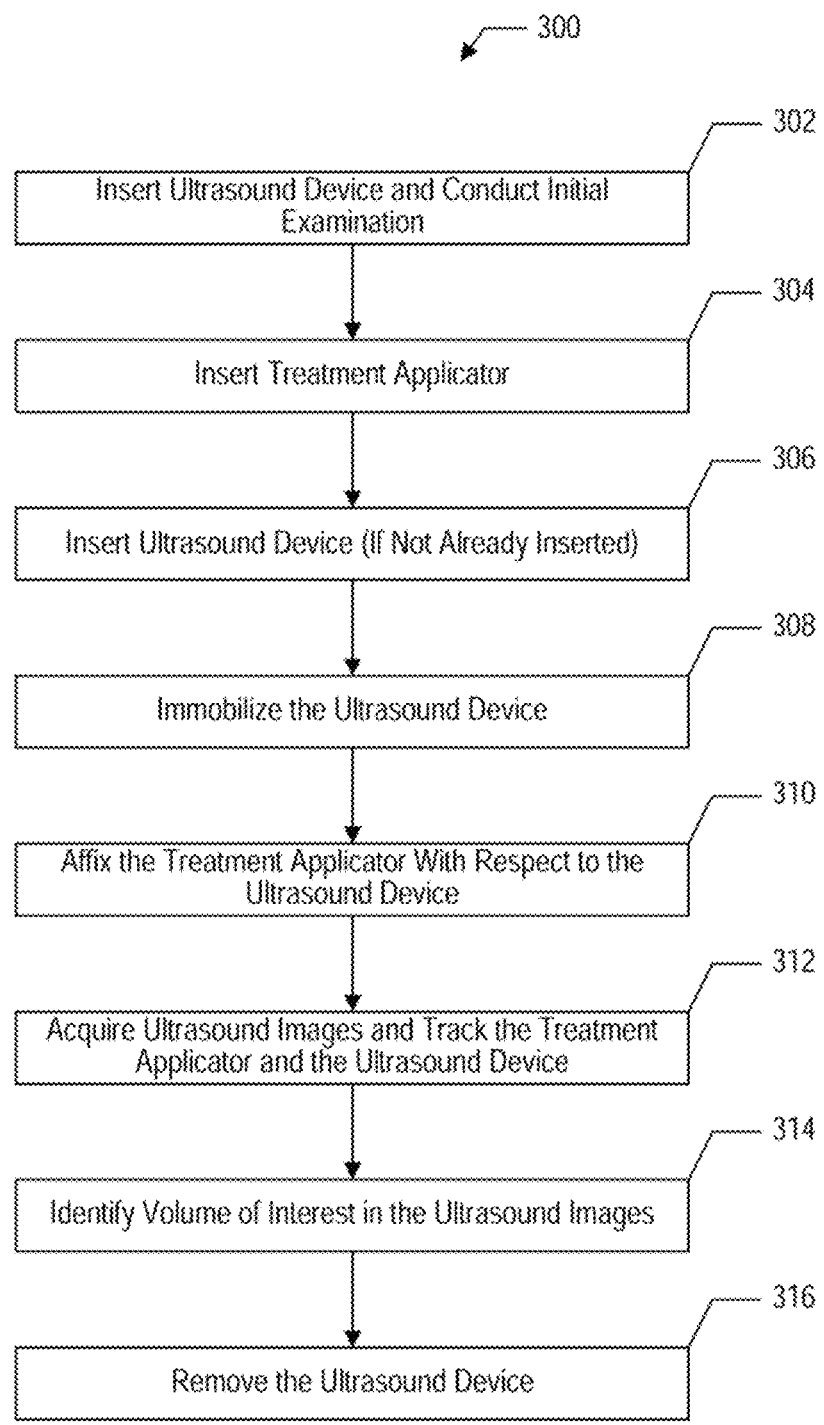
FIG. 3 depicts a flow chart of an exemplary process for acquiring ultrasound image data for brachytherapy treatment planning, according to an embodiment.
Figure 4:
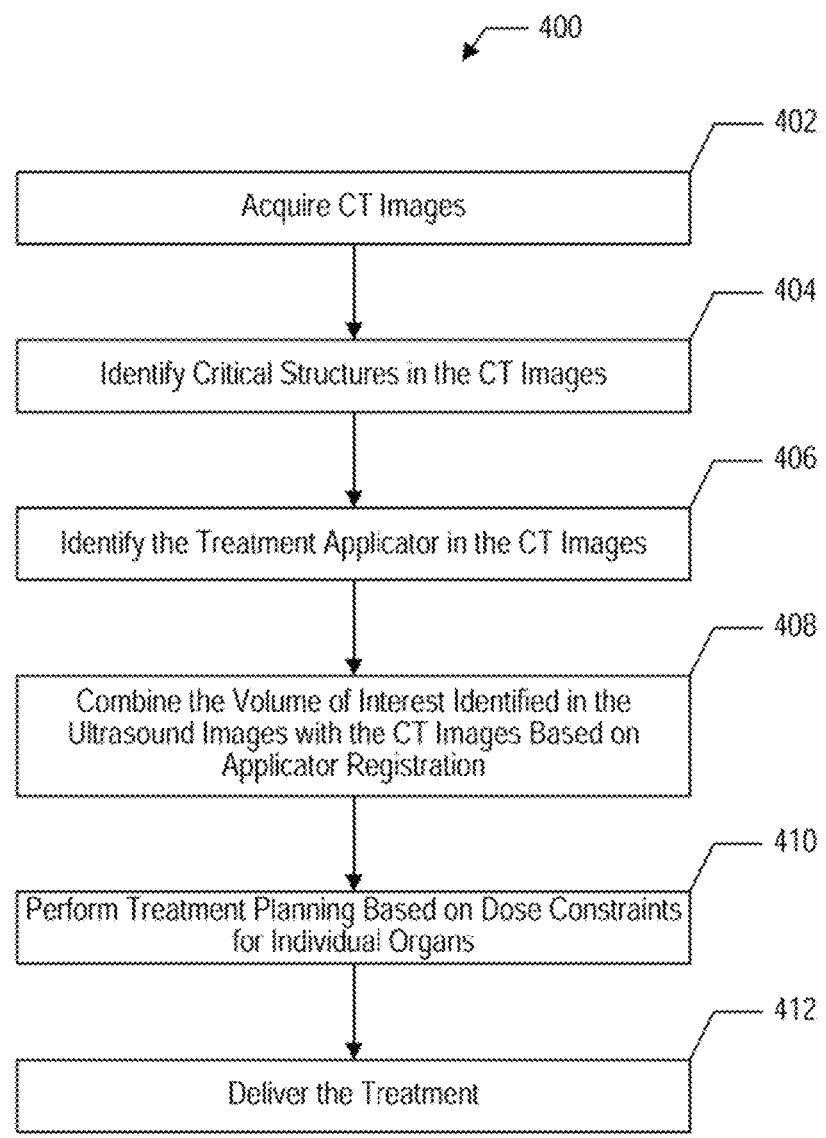
FIG. 4 depicts a flow chart of an exemplary process for combining the ultrasound image data with CT image data for brachytherapy treatment planning, according to an embodiment.

FIGS. 3 and 4 illustrate flowcharts of exemplary processes 300 and 400 for radiation treatment planning using ultrasound image data, according to additional embodiments. Processes 300 and 400 may be carried out in connection with the radiation treatment planning system of FIG. 1. Processes 300 and 400 may be carried out individually or as a combined process with process 300 preceding process 400.

According to process 300, at step 302, the ultrasound device is inserted into the patient. An initial examination of the patient is conducted using the ultrasound device. The initial examination allows the physician to determine anatomy, a target region, and/or a pathology within the patient and design a proper procedure for inserting the treatment applicator, such as the brachytherapy applicator, catheter, needles, or other implant devices.

Figure 5A:
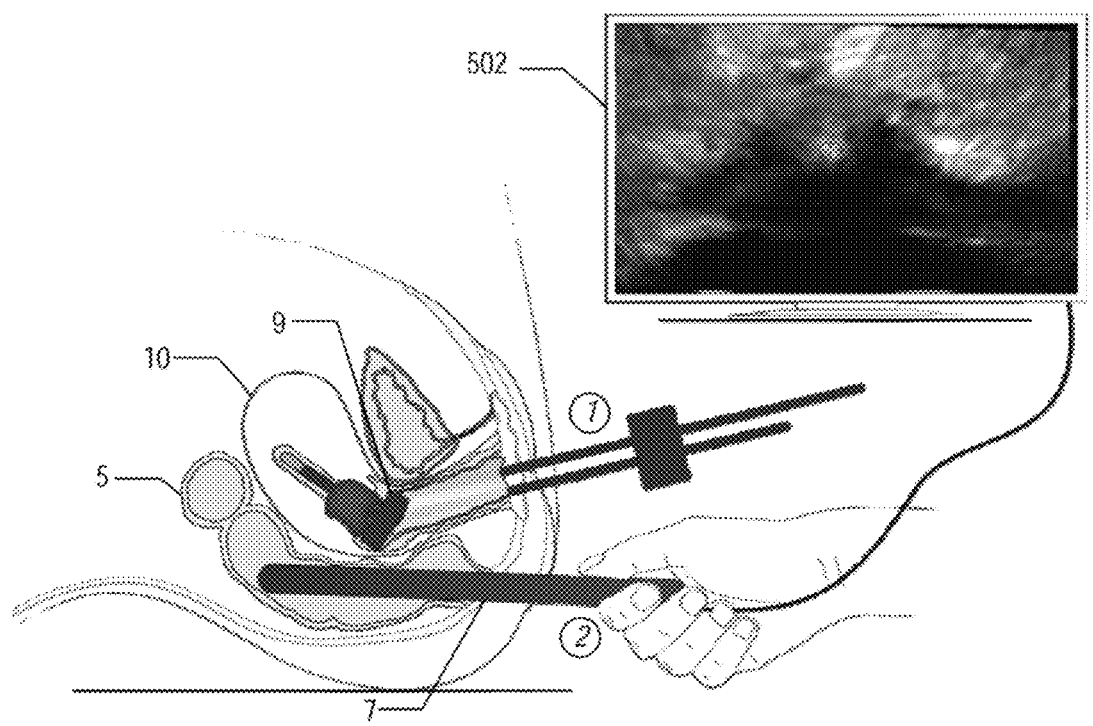
FIGS. 5A-5F depict schematic diagrams of the exemplary operational steps applied to the system of FIG. 1 during the brachytherapy treatment planning, according to some embodiments.

At step 304, the applicator may be placed in a targeted region of the patient. For example, as shown in FIG. 5A, in a patient with a cervical cancer, the brachytherapy applicator may be inserted into the patient through the skin or through the vagina using standard brachytherapy techniques. The applicator may be a tandem-and-ovoid or tandem-and-ring applicator that is placed in cervical cavity 10 of the patient and is secured to the patient by, e.g., gauze packing. Initial images 502, such as ultrasound images or X-ray images, may be taken to monitor the placement of the tandem of the applicator.

At step 306, after the treatment applicator is properly placed in the targeted region of the patient, the ultrasound device is placed inside the patient or secured outside the patient, if it is not already placed at step 302. As shown in FIG. 5A, for a patient with a cervical cancer, the ultrasound device may be inserted in rectum 5 of the patient. Again, initial images 502 may be acquired to ensure the ultrasound device is placed properly within the patient.

As step 308, the ultrasound device may be immobilized and secured to base 3. The ultrasound device may be immobilized by a fastener, such as a bolt, a screw, a clamp, or other mechanisms, to secure it to extension arm 4, as discussed above. In the illustrated embodiment, at step 310, the treatment applicator may be affixed with respect to ultrasound device either through base 3 or other supporting structures. However, in other embodiments, step 310 may be omitted.

Figure 5B:
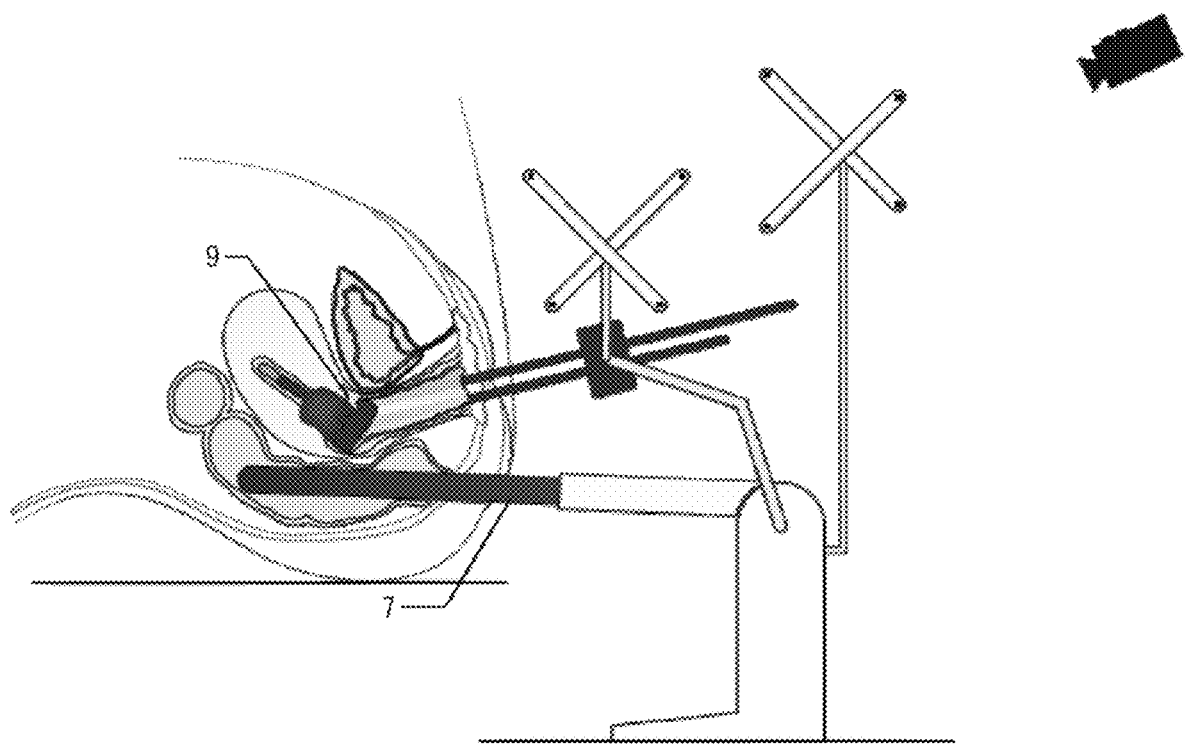

FIG. 5B illustrates an exemplary embodiment of the system after the ultrasound device and the applicator are immobilized and affixed to base 3. The structure that immobilizes the ultrasound device and the applicator is not limited to those discussed above. Any supporting structures that may maintain the positions of the ultrasound device and the applicator during the acquisition of the ultrasound images may be adopted.

Figure 5C:
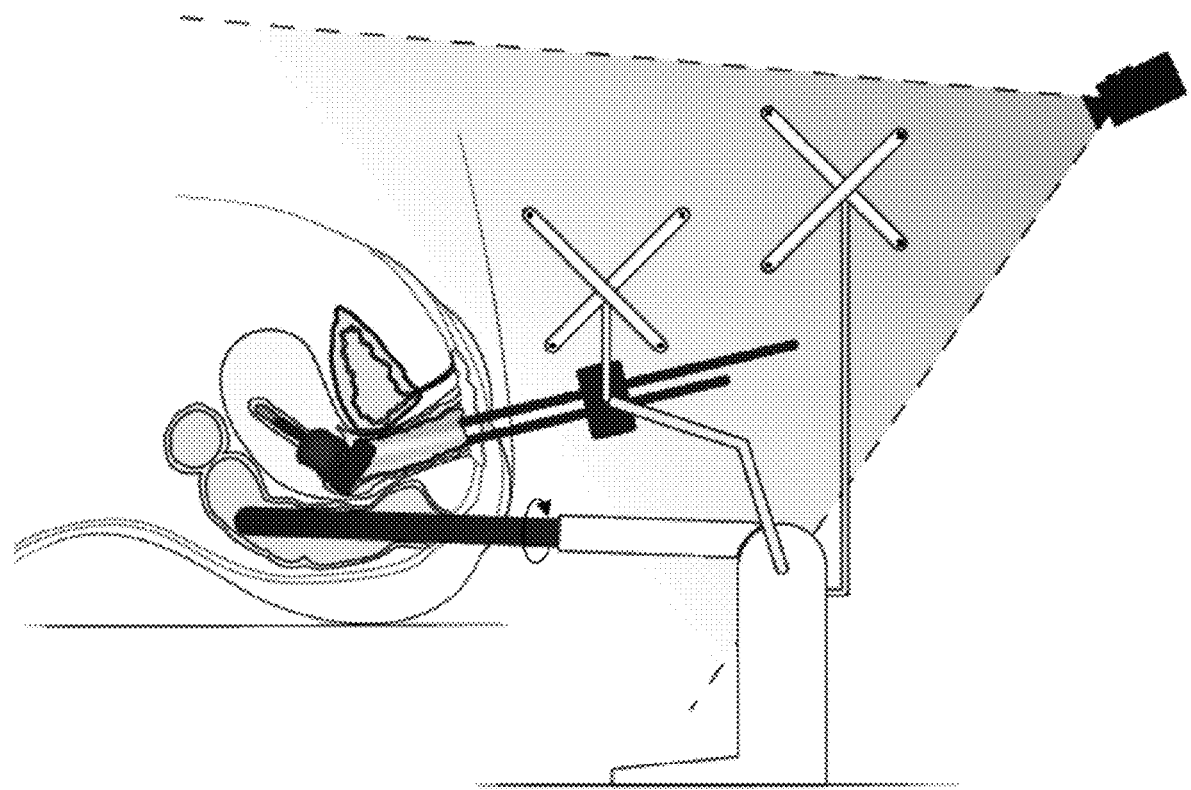
Figure 5D:
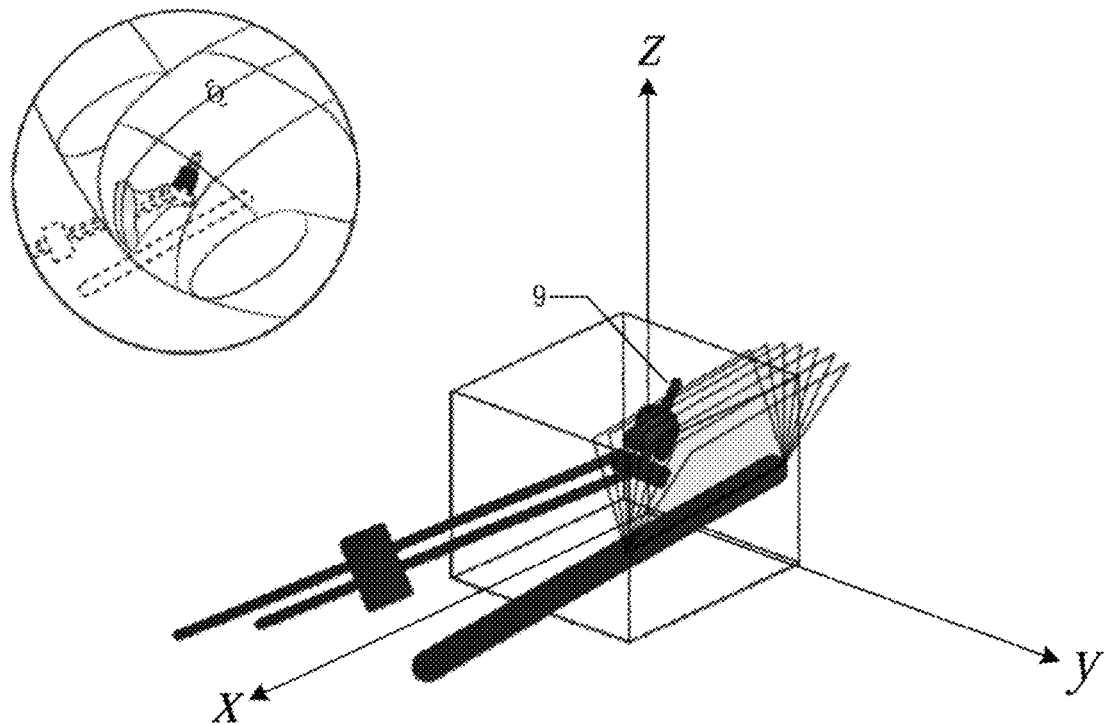

At step 312, a set of ultrasound images are acquired by rotating the ultrasound device. In addition, the positions of the applicator and the ultrasound device are tracked just before and/or during the acquisition of the ultrasound images. As shown in FIG. 5C, the ultrasound device may be rotated by the motor placed in extension arm. The applicator and the ultrasound device may be tracked by a tracking device that tracks the markers associated with the applicator and the ultrasound device. In addition, the rotational angle of the ultrasound device may be tracked by the encoder of the motor that drives the ultrasound device or by the markers placed on the external surface of the ultrasound device. FIG. 5D illustrates a set of ultrasound image slides that form a three-dimensional data set generated by the ultrasound device and their spatial relationships with the applicator.

At step 314, the boundary of target tissue (also called the target volume) is identified in the ultrasound images. A process similar to that shown in FIG. 9 may be carried out to identify the volume of interest that includes the target tissue. This target volume is also called high risk clinical tumor volume (HR-CTV). In addition, the location of the applicator in the ultrasound images may be determined based on the tracking information provided by the tracking device. A graphical representation of the applicator may be projected onto the ultrasound data as shown in FIG. 8.

Figure 5E:
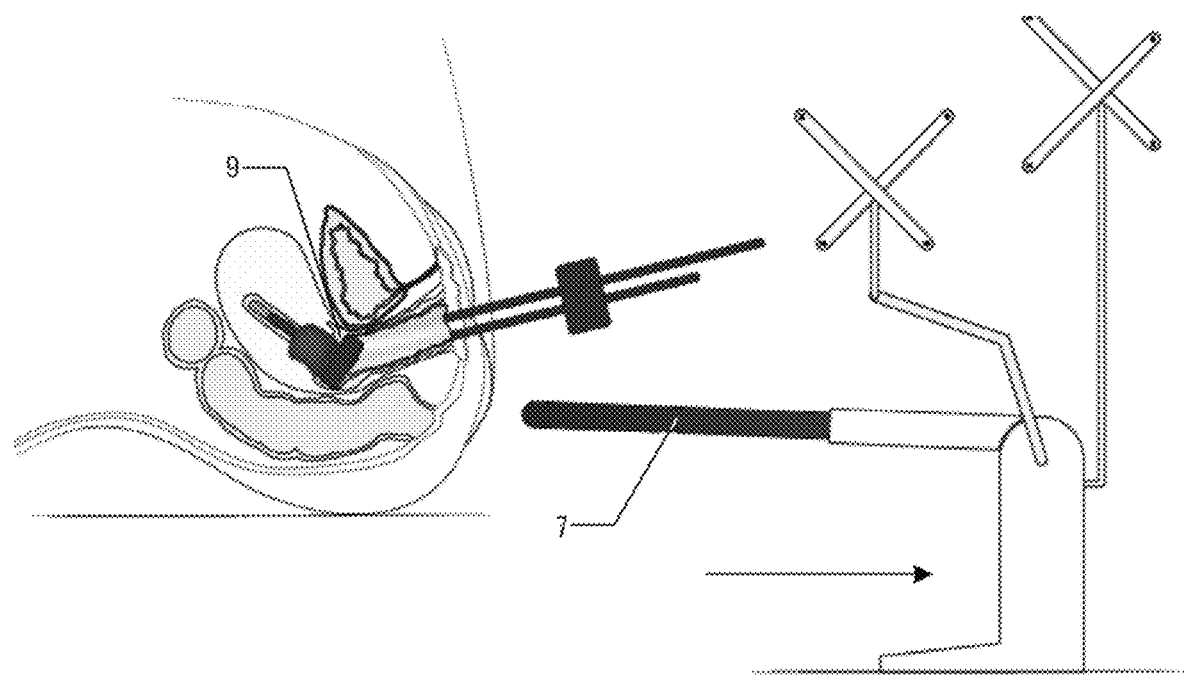

At step 316, the ultrasound device is removed from the patient. As shown in FIG. 5E, the marker is dismounted from the applicator. The ultrasound device is then disconnected from the patient. Thereafter, the patient may be transported and connected to a second imaging device, such as a CT device or an X-ray machine, so that process 400 is carried out.

According to process 400, at step 402, a set of CT images are acquired from the CT device. At step 404, critical structures, such as the organs at risk, are identified by analyzing the CT images. At step 406, the applicator, or another landmark feature (e.g., another device positioned within the patient), is identified by analyzing the CT images. In the description contained herein, the embodiment in which the applicator is used for registration is described. However, presently contemplated embodiments include use of other landmark features, such as other medical devices used in a given procedure, a marker on or inside the patient's anatomy (e.g., the patient's hip), a reference coordinate system in the operating room, or any other recognizable point in the image data sets, for image registration.

Graphical boundaries of the critical structures and the graphical representation of the applicator may be projected onto the CT images. Steps 402, 404, and 406 may be performed as part of step 206 in FIG. 2 or as separate steps. For example, steps 404 and 406 may be performed after the second set of image data is obtained at step 206. Steps 404 and 406 may be performed on the same imaging system or device used to obtain the second image data set or on a different treatment planning system, such as subsystem 19 of FIG. 1.

Figure 5F:
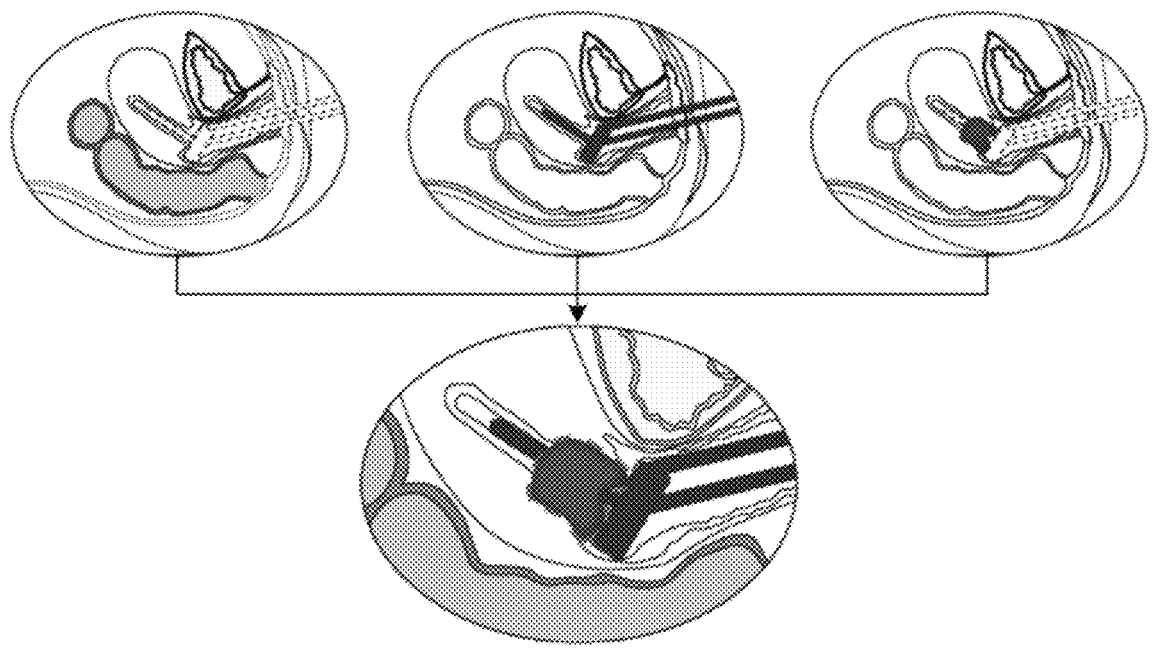

At step 408, the volume of interest including the target tissue identified in the ultrasound images may be combined with the CT images based on the applicator registration, or registration of another landmark feature. The applicator registration may be carried out automatically by subsystem 19 or based on user inputs to subsystem 19. After the graphical representations of the applicator in the ultrasound image data and the CT image data are aligned, the volume of interest in the ultrasound image data may be projected on or in the CT image data. FIG. 5F illustrates an exemplary process of projecting a graphical boundary of the target tissue onto the CT images that includes the graphical boundaries of the critical structures. As shown in FIG. 5F, the resulting combination includes graphical representations of both the critical structures and the target tissue.

At step 410, treatment planning is performed based on the combined image data and the dose constraints for individual organs. The treatment planning information similar to that shown in FIG. 14 may be generated based on the combined image data and the treatment parameters. The physician may then determine the treatment procedures and parameters based on the treatment planning information. At step 412, the treatment is then carried out based on the treatment planning information.

According to an alternative embodiment, the CT image data in process 400 may be replaced by X-ray image data. The X-ray image data may be acquired by conventional X-ray device, such as a C-arm machine. The X-ray image data may include a plurality of X-ray images of the targeted region of the patient taken in orthogonal, semi-orthogonal, or variable angles. The X-ray image data are then processed by subsystem 19 to identify a graphical representation of the applicator and other anatomical structures that have relatively high contrasts. The anatomical structures identified in the X-ray image data may include, for example, bladder balloon, vaginal packing, marking devices inserted into organs, contrast material, applicators, bony structures, and other organs at risk.

The graphical representation of the applicator projected in the ultrasound image data in process 300 may then be registered with the graphical representation of the applicator identified in the X-ray image data. Once the images of the applicator are aligned, the ultrasound image data generated in process 300 including the graphical boundary of the target tissue may then be projected to the X-ray image data using the techniques discussed above. As a result, the combined image data may include the graphical boundary identifying the target tissue determined based on the ultrasound image data and the graphical boundaries identifying the surrounding organs determined based on the X-ray image data. The combined image data may then be used for radiation therapy treatment planning using the similar techniques disclosed above.

By replacing the CT image data with the X-ray image data, this embodiment may further reduces the costs of the system for conducting radiation therapy treatment procedure. Because many developing countries or underdeveloped areas only have access to conventional X-ray machines, this embodiment may be widely adopted for radiation therapy treatment planning in those countries or areas.

Moreover, while illustrative embodiments have been described herein, the scope of thereof includes any and all embodiments having equivalent elements, modifications, omissions, combinations (e.g., of aspects across various embodiments), adaptations and/or alterations as would be appreciated by those in the art based on the present disclosure. For example, the number and orientation of components shown in the exemplary systems may be modified. Further, with respect to the exemplary methods illustrated in the attached drawings, the order and sequence of steps may be modified, and steps may be added or deleted. For example, the identification of the volume of interest in the ultrasound image data at step 314 may be performed out of the order shown in FIG. 3 and may be performed at any point prior to combining the imagines based on the applicator registration at step 408.

The claims are to be interpreted broadly based on the language employed in the claims and not limited to examples described in the present specification, which examples are to be construed as non-exclusive. Further, the steps of the disclosed methods may be modified in any manner, including by reordering steps and/or inserting or deleting steps.

It is intended, therefore, that the specification and examples be considered as exemplary only. Additional embodiments are within the purview of the present disclosure.

The invention claimed is:

1. A method for generating radiation therapy treatment plan information for a radiation therapy treatment plan by using ultrasound images, the method comprising:
   obtaining, via an ultrasound device affixed to a support structure, a first set of image data representing a first image of an anatomical region of a patient, wherein the anatomical region includes a treatment applicator inserted into the anatomical region, the treatment applicator being affixed to the anatomical region and to the support structure configured to provide a fixed spatial relationship between the treatment applicator and the ultrasound device;
   determining a position of the treatment applicator as represented in the first set of image data based on tracking information and the fixed spatial relationship;
   obtaining a second set of image data representing a second image of the anatomical region;
   determining a position of the treatment applicator as represented in the second set of image data;
   combining at least a portion of the first set of image data with the second set of image data based on the position of the treatment applicator in the first and second sets of image data, wherein one of the first set and the second set of image data is used to identify a target tissue portion in the anatomical region; and
   generating, based on the combined image data, the treatment plan information for treating the target tissue portion in the anatomical region.

2. The method of claim 1, further comprising:
   receiving a first identification of a landmark feature in the first image;
   receiving a second identification of the landmark feature in the second image;
   aligning the first identification of the landmark feature in the first image with the second identification of the landmark feature in the second image, such that the position of the landmark feature represented in the first image is aligned with the position of the landmark feature represented in the second image; and combining at least a portion of the first set of image data with at least a portion of the second set of image data based on the aligned landmark feature in the first and second images.

3. The method of claim 2, wherein the landmark feature comprises the treatment applicator.

4. The method of claim 2, wherein the combining at least a portion of the first set of image data with at least a portion of the second set of image data based on the aligned landmark feature in the first and second images further comprises: identifying, in the second image data, the position of the target tissue portion represented in the first image.

5. The method of claim 1, further comprising receiving tracking information of a position of the ultrasound device during the obtaining of the first set of image data.

6. The method of claim 5, further comprising fixing a location of the ultrasound device and the treatment applicator with respect to a reference during the obtaining the first set of image data.

7. The method of claim 5, further comprising receiving the tracking information from at least one of an optical tracking system, a magnetic tracking system, an electromagnetic tracking system, or a motor having an encoder.

8. The method of claim 1, further comprising receiving an identification of a boundary of the target tissue portion in the anatomical region based on the first image.

9. The method of claim 8, further comprising:
displaying, via a display device, the first image; and
receiving a user selection identifying the target tissue portion in the first image.

10. The method of claim 9, wherein the user selection specifies a graphical boundary of the identified target tissue portion.

11. The method of claim 10, wherein the combining of the portion of the first set of image data with the second set of image data further comprises combining the boundary of the target tissue portion identified in the first image with the second set of image data according to the position of the treatment applicator.

12. The method of claim 1, wherein the treatment applicator includes a brachytherapy applicator.

13. The method of claim 1, wherein the anatomical region includes one of a cervix, a prostate, or a breast.

14. A system for generating radiation therapy treatment plan information for a radiation therapy treatment plan by using ultrasound images, the system comprising:
an ultrasound device configured to generate a first set of image data representing a first image of an anatomical region of a patient, wherein the anatomical region includes a treatment applicator inserted into the anatomical region, the treatment applicator being affixed to the anatomical region;
a support structure affixed to the ultrasound device and the treatment applicator, the support structure configured to provide a fixed spatial relationship between the treatment applicator and the ultrasound device and maintain a position of the treatment applicator and a position of the ultrasound device with respect to a reference when the ultrasound device generates the first set of image data;
a tracking device configured to generate tracking information indicating a position of the treatment applicator as represented in the first set of image data; and
a processor configured to:
obtain the first set of image data from the ultrasound device;
receive the tracking information from the tracking device;
determine a position of the treatment applicator as represented in the first set of image data based on the tracking information and the fixed spatial relationship;
obtain, from an imaging device, a second set of image data representing a second image of the anatomical region;
determine a position of the treatment applicator as represented in the second set of image data;
combine at least a portion of the first set of image data with the second set of image data based on the position of the treatment applicator in the first and second sets of image data, wherein the combined image data is used to identify a target tissue portion in the anatomical region; and
generate, based on the combined image data, the treatment plan information for treating the target tissue portion in the anatomical region.

15. The system of claim 14, wherein the treatment applicator is disposed in a gynecological area of the patient and the ultrasound device is placed in a trans-rectal position of the patient, a transabdominal position of the patient, or a combination thereof.

16. The system of claim 14, further comprising:
a display device configured to display the first image to a user;
a user input device configured to receive user input identifying the target tissue portion in the first image.

17. The system of claim 14, wherein the tracking device generates the tracking information based on at least one of optical signals, magnetic signals, or electrical systems.

18. The system of claim 17, wherein the tracking device includes a motor having an encoder.

19. The system of claim 18, wherein:
the motor is coupled with the ultrasound device and configured to rotate the ultrasound device; and
the encoder is configured to generate tracking information of a rotational angle of the ultrasound device when the ultrasound device generates the first set of image data.

20. The system of claim 14, wherein the ultrasound device includes a three-dimensional matrix probe.

21. A non-transitory computer-readable medium storing instructions, which, when executed by a processor, cause the processor to perform a method for generating radiation therapy treatment information for a radiation therapy treatment plan by using ultrasound images, the method comprising:
obtaining, via an ultrasound device affixed to a support structure, a first set of image data representing a first image of an anatomical region of a patient, wherein the anatomical region includes a treatment applicator inserted into the anatomical region, the treatment applicator being affixed to the anatomical region and to the support structure configured to provide a fixed spatial relationship between the treatment applicator and the ultrasound device;
determining a position of the treatment applicator as represented in the first set of image data based on tracking information and the fixed spatial relationship;
obtaining a second set of image data representing a second image of the anatomical region;

determining a position of the treatment applicator as represented in the second set of image data;

combining at least a portion of the first set of image data with the second set of image data based on the position of the treatment applicator in the first and second sets of image data, wherein the combined image data is used to identify a target tissue portion in the anatomical region; and generating, based on the combined image data, the treatment plan information for treating the target tissue portion in the anatomical region.

22. A method for generating radiation therapy treatment information for a radiation therapy treatment plan by using ultrasound images, the method comprising:

obtaining, via an ultrasound device affixed to a support structure, a first set of image data representing a first image of an anatomical region of a patient, wherein the anatomical region includes a treatment applicator inserted into the anatomical region and incorporates a landmark feature, the treatment applicator being affixed to the anatomical region and to the support structure configured to provide a fixed spatial relationship between the treatment applicator and the ultrasound device;

determining a position of the landmark feature as represented in the first set of image data based on tracking information and the fixed spatial relationship;

obtaining a second set of image data representing a second image of the anatomical region and including a second position of the landmark feature;

determining a position of the treatment applicator as represented in the second set of image data;

combining at least a portion of the first set of image data with the second set of image data based on the position of the landmark feature in the first set of image data and the second position of the landmark feature in the second set of image data, wherein one of the first set and the second set of image data is used to identify a target tissue portion in the anatomical region; and generating, based on the combined image data, the treatment plan information for treating the target tissue portion in the anatomical region.

23. The method of claim 22, further comprising receiving tracking information of a position of the ultrasound device during the obtaining of the first set of image data.

24. The method of claim 23, further comprising fixing a location of the ultrasound device and the landmark feature with respect to a reference during the obtaining the first set of image data.

25. The method of claim 22, further comprising receiving an identification of a boundary of the target tissue portion in the anatomical region based on the first image.

26. The method of claim 25, further comprising:
displaying, via a display device, the first image; and
receiving a user selection identifying the target tissue portion in the first image.

27. The method of claim 26, wherein the user selection specifies a graphical boundary of the identified target tissue portion.

28. The method of claim 27, wherein the combining of the portion of the first set of image data with the second set of image data further comprises combining the boundary of the target tissue portion identified in the first image with the second set of image data according to the position and the second position of the landmark feature.

29. The method of claim 22, wherein the landmark feature includes a brachytherapy applicator.

* * * * *